US010285401B2

(12) United States Patent
McSherry et al.

(10) Patent No.: US 10,285,401 B2
(45) Date of Patent: May 14, 2019

(54) SELF INDICATING ANTIMICROBIAL CHEMISTRY

(71) Applicant: Ecolab USA Inc., Saint Paul, MN (US)

(72) Inventors: David D. McSherry, St. Paul, MN (US); Junzhong Li, Eagan, MN (US); Richard Staub, Lakeville, MN (US)

(73) Assignee: Ecolab USA Inc., Saint Paul, MN (US)

( * ) Notice: Subject to any disclaimer, the term of this patent is extended or adjusted under 35 U.S.C. 154(b) by 167 days.

(21) Appl. No.: 15/260,760

(22) Filed: Sep. 9, 2016

(65) Prior Publication Data

US 2017/0071200 A1 Mar. 16, 2017

Related U.S. Application Data

(60) Provisional application No. 62/216,435, filed on Sep. 10, 2015.

(51) Int. Cl.
*A01N 37/16* (2006.01)
*C12Q 1/28* (2006.01)
*C12Q 1/22* (2006.01)
*A01N 25/02* (2006.01)

(52) U.S. Cl.
CPC ............ *A01N 37/16* (2013.01); *A01N 25/02* (2013.01); *C12Q 1/22* (2013.01); *C12Q 1/28* (2013.01); *C12Y 111/01007* (2013.01); *G01N 2333/908* (2013.01)

(58) Field of Classification Search
None
See application file for complete search history.

(56) References Cited

U.S. PATENT DOCUMENTS

| | | | |
|---|---|---|---|
| 4,278,615 A * | 7/1981 | Stober | C07C 407/00 562/2 |
| 4,279,993 A | 7/1981 | Magers et al. | |
| 4,385,114 A | 5/1983 | Guthlein et al. | |
| 4,794,079 A | 12/1988 | Buckler et al. | |
| 4,900,682 A | 2/1990 | Fischer et al. | |
| 4,908,323 A | 3/1990 | Werner | |
| 4,996,332 A | 2/1991 | Buckler et al. | |
| 5,081,044 A | 1/1992 | Buckler et al. | |
| 5,246,620 A | 9/1993 | Gethoffer et al. | |
| 5,266,587 A | 11/1993 | Sankey et al. | |
| 5,391,324 A | 2/1995 | Reinhardt et al. | |
| 5,422,028 A | 6/1995 | Oakes et al. | |
| 5,463,112 A | 10/1995 | Sankey et al. | |
| 5,466,825 A | 11/1995 | Carr et al. | |
| 5,576,282 A | 11/1996 | Miracle et al. | |
| 5,616,281 A | 4/1997 | Hardy et al. | |
| 5,718,910 A | 2/1998 | Oakes et al. | |
| 5,817,614 A | 10/1998 | Miracle et al. | |
| 5,914,303 A | 6/1999 | Sankey et al. | |
| 5,928,382 A | 7/1999 | Reinhardt et al. | |
| 6,211,237 B1 | 4/2001 | Huss et al. | |
| 6,262,013 B1 | 7/2001 | Smith et al. | |
| 6,274,542 B1 | 8/2001 | Carr et al. | |
| 6,537,958 B1 | 3/2003 | Di Capua et al. | |
| 6,548,467 B2 | 4/2003 | Baker et al. | |
| 6,548,470 B1 | 4/2003 | De Buzzaccarini et al. | |
| 6,693,069 B2 | 2/2004 | Korber et al. | |
| 6,841,090 B1 | 1/2005 | Serego Allighieri et al. | |
| 6,861,262 B2 | 3/2005 | Novinski et al. | |
| 7,445,908 B2 | 11/2008 | Paul | |
| 7,494,963 B2 | 2/2009 | Ahmed et al. | |
| 7,682,403 B2 | 3/2010 | Gohl et al. | |
| 7,829,020 B2 | 11/2010 | Pagoria et al. | |
| 8,110,603 B2 | 2/2012 | Kawabata et al. | |
| 8,426,634 B2 | 4/2013 | Neas et al. | |
| 8,729,296 B2 | 5/2014 | Fast et al. | |
| 8,828,910 B2 | 9/2014 | Aksela et al. | |
| 9,012,504 B2 | 4/2015 | Olson et al. | |
| 9,034,390 B2 | 5/2015 | Kielbania, Jr. | |
| 9,244,016 B2 | 1/2016 | Karato et al. | |
| 9,288,992 B2 | 3/2016 | Li et al. | |

(Continued)

FOREIGN PATENT DOCUMENTS

DE 19651797 A1 6/1998
EP 0231632 A2 8/1987

(Continued)

OTHER PUBLICATIONS

National Center for Biotechnology Information. PubChem Compound Database; CID=41206, https://pubchem.ncbi.nlm.nih.gov/compound/41206 (accessed Aug. 30, 2018).*
National Center for Biotechnology Information. PubChem Compound Database; CID=19700, https://pubchem.ncbi.nlm.nih.gov/compound/19700 (accessed Aug. 30, 2018).*
Minning, Stefan, et al., "Determination of peracid and putative enzymatic peracid formation by an easy colorimetric assay", Analytica Chimica Acta, (1999), pp. 293-298.
Pinkernell, Ulrich, et al., "Selective Photometric Determination of Peroxycarboxylic Acids in the Presence of Hydrogen Peroxide", Analyst, (Jun. 1997), vol. 122, pp. 567-571.
Harms, Diedrich, et al., "Rapid and selective determination of peroxyacetic acid in disinfectants using flow injection analysis", Analytica Chimica Acta, (1999), pp. 233-238.

(Continued)

*Primary Examiner* — Jeffrey T. Palenik
(74) *Attorney, Agent, or Firm* — McKee, Voorhees & Sease, PLC

(57) ABSTRACT

Self-indicating chemistries are provided for visual detection by a user of efficacious levels of peroxycarboxylic acid concentrations in a solution produced in situ. The self-indicating chemistries include a combination of dyes providing a visual color indication, such as a tri-color indicator system, such as a yellow, green, and red color system indicating in situ threshold levels of peroxycarboxylic acid concentrations in a solution employing the self-indicating chemistry. Systems, kits and compositions for a quantitative assessment of an in situ perhydrolysis reaction to generate peroxycarboxylic acids are provided. Methods of use are further provided.

8 Claims, 3 Drawing Sheets

(56) References Cited

U.S. PATENT DOCUMENTS

| | | | |
|---|---|---|---|
| 9,321,664 B2 | 4/2016 | Li et al. | |
| 9,585,397 B2 | 3/2017 | Li et al. | |
| 9,676,711 B2 | 6/2017 | Junzhong et al. | |
| 9,701,931 B2 | 7/2017 | Moore | |
| 9,752,105 B2 | 9/2017 | Stokes et al. | |
| 2002/0119743 A1* | 8/2002 | Hilgren | A01N 37/16 452/71 |
| 2002/0161258 A1 | 10/2002 | Miracle et al. | |
| 2007/0093407 A1 | 4/2007 | Bianchetti et al. | |
| 2007/0274857 A1 | 11/2007 | Okano et al. | |
| 2011/0217761 A1* | 9/2011 | Hilgren | A62D 3/02 435/262 |
| 2012/0122979 A1 | 5/2012 | Dicosimo et al. | |
| 2012/0164236 A1 | 6/2012 | Iwasa et al. | |
| 2013/0018099 A1* | 1/2013 | McSherry | A01N 37/16 514/557 |
| 2013/0247308 A1 | 9/2013 | Duerrschmidt et al. | |
| 2014/0097144 A1* | 4/2014 | Li | C11D 3/394 210/747.5 |
| 2014/0120179 A1 | 5/2014 | Smith et al. | |
| 2014/0121272 A1 | 5/2014 | Smith et al. | |
| 2017/0020130 A1 | 1/2017 | Buschmann et al. | |
| 2017/0064949 A1 | 3/2017 | Kraus et al. | |

FOREIGN PATENT DOCUMENTS

| | | |
|---|---|---|
| EP | 1114137 B1 | 7/2004 |
| EP | 1129171 B1 | 8/2005 |
| EP | 1926808 B1 | 7/2011 |
| EP | 2471941 B1 | 9/2015 |
| EP | 2714877 B1 | 7/2017 |
| EP | 2566943 B1 | 9/2017 |
| WO | 9002339 A1 | 3/1990 |
| WO | 9222806 A1 | 12/1992 |
| WO | 9504128 A1 | 2/1995 |
| WO | 9524933 A1 | 9/1995 |
| WO | 9533816 A1 | 12/1995 |
| WO | 9804659 A3 | 2/1998 |
| WO | 2012090124 A1 | 7/2012 |
| WO | 2015118357 A2 | 8/2015 |
| WO | 2016100694 A1 | 6/2016 |
| WO | 2016100700 A1 | 6/2016 |
| WO | 2017007416 A1 | 1/2017 |
| WO | 2017044806 A1 | 3/2017 |

OTHER PUBLICATIONS

"Determination of Peracetic Acid (PAA) and Hydrogen Peroxide ($H2O2$) in Water", Application Note, Hach Company, (2014), 2 pages, retrieved from the Internet.

"Determination of peracids in the presence of large excess of hydrogen peroxide using a rapid and convenient spectrophotometric method." Analyst vol. 113 (1998), No. 9, pp. 1477-1479.

"International Search Report and the Written Opinion of the International Searching Authority", International Application No. PCT/US2016/051041, 16 pages, dated Dec. 11, 2016.

Ascione et al., "Quantitative Determination of Gallamine Triethiodide", Journal of Pharmaceutical Sciences, vol. 57. No. 10, pp. 1768-1770, Oct 1968.

* cited by examiner

SELF INDICATING ANTIMICROBIAL CHEMISTRY

RELATED APPLICATIONS

This application claims priority to U.S. Provisional Application Ser. No. 62/216,435 filed on Sep. 10, 2015 entitled "2-Part Self Indicating Antimicrobial Chemistry," the entire disclosure of which are incorporated herein by reference.

FIELD OF THE INVENTION

The invention relates to a self-indicating chemistry suitable for detecting efficacious levels of peroxycarboxylic acid concentrations, namely for surface disinfection, in a solution in situ. In particular, a combination of dyes, namely a combination of at least two or three dyes to provide a tri-color indicator system. In an aspect, the tri-color indicators are suitable for providing a series of yellow, green, and red colors to indicate threshold levels of peroxycarboxylic acid concentrations in a solution. The self-indicating chemistry compositions provide a proof of generation or proof of delivery of the peroxycarboxylic acid compositions employing the self-indicating chemistry compositions. Beneficially, the self-indicating chemistry compositions are non-catalytic and non-fluorescent. Methods of use are provided.

BACKGROUND OF THE INVENTION

Among various biocides known, peroxycarboxylic acids are increasingly used as antimicrobials and bleaching agents in many applications, owing to their high efficacy against a broad spectrum of microorganisms, color safe property, low residues and nontoxic nature of their decomposition products. Peracetic acid is the most commonly used peroxycarboxylic acid and has been shown to be a good biocide, but only at relatively high concentrations (generally greater than 80 part per million). Similarly, peroxyfatty acids have also been shown to be biocidal, but only at high concentrations (greater than 200 ppm). In contrast, peroxyformic acid has an advantageous degree and range of microcidal properties compared to other peroxycarboxylic acids, such as peracetic and perproprionic acids, as disclosed by V. Merka et al in J. Hyg. Epidem, Microbiol. Immunol., 1965 (IX) 220, as well as in European Patent Application No. 863,098,96, which are incorporated herein by reference in their entirety.

Most often, peroxycarboxylic acids are generated in a chemical plant through an acid catalyzed equilibrium reaction, and then shipped to customers for on-site use. Due to the limited storage stability of peroxycarboxylic acids, the peroxycarboxylic acids must be packed in special containers and shipped under strict Department of Transportation (DOT) guidelines. Further, excess amounts of reagents (e.g., acids, oxidizing agents, and stabilizers) are present in these compositions during shipping to prevent decomposition. For certain peroxycarboxylic acids, such as peroxyformic acid, however, the inherent instability of the substance relative to the higher alkyl peracids, and the explosive nature of the substance at the concentrate make it an even more significant challenge to be manufactured, stored and transported before dilution prior to use, in the similar way like higher alkyl peracids. Accordingly, peroxycarboxylic acids have alternatively been generated in situ through a perhydrolysis reaction of the higher alkyl carboxylic acid esters of polyhydric alcohol under strong alkaline conditions (e.g. pH greater than 12) and thereafter acidified to become an efficient biocide, as disclosed in the Patent Application No. WO2012/090124 and U.S. Pat. No. 7,919,122, each of which are incorporated herein by reference in their entirety.

Such in situ generation of peroxycarboxylic acid biocides are thereafter suitable for use when a sufficient concentration biocide is achieved. However, certain assays for peroxycarboxylic acid compositions are destructive to the biocide concentration and therefore undesirable. For example, iodide is a destructive assay, as disclosed for example in U.S. Pat. No. 4,900,682. Moreover, other fluorescent tracers may be destructive to peracid compositions. Fluorometric spectroscopy concerns the detection of fluorescent light emitted by a sample and involves using a beam of light, usually ultraviolet (UV) light, that excites the electrons in molecules of certain compounds in the sample and causes them to emit light of a lower energy (i.e., to "fluoresce"). There are several types of fluorometers for measuring emitted fluorescence. Fluorometers generally have of a source of excitation radiant energy, an excitation wavelength selector, a sample cell to contain the sample material, an emission wavelength selector, a detector with signal processor and a readout device. Filter fluorometers use optical filters to isolate the incident light and fluorescent light. Spectrofluorometers use diffraction grating monochromators to isolate the incident light and fluorescent light. One method of monitoring the concentration of a chemical product (e.g., a cleaning agent) within a water sample relies on monitoring the fluorescence of the product that occurs when the sample (and the product within the sample) is exposed to a predetermined wavelength of light. Accordingly, the use of fluorescent actives often requires use of optical measuring devices. However it may be more desirable to have a built-in quantitative measurement system as opposed to requiring a device, such as controller modules or other handheld devices.

Accordingly, it is an objective of the invention to develop self-indicating systems for use with on-site generation of peroxycarboxylic acids to provide a visual indicator of peroxycarboxylic concentration without destroying the peroxycarboxylic acid, including for example peroxyformic acids. In a further aspect, the invention is suitable for providing a visual indicator that further provides a stabilizing effect on the peroxycarboxylic acid as opposed to a destructive effect.

A further object of the invention is to provide a method of indicating completion of a peroxycarboxylic acid generated by perhydrolysis in situ through a visual indication to a user, including a non-fluorescent marker or indicator, and a non-catalytic or destructive indicator.

It further is an object of this invention to provide for a quick visual screening procedure to screen and test toxicants and biocides useful in control of microorganism growth and provide for control or elimination of microorganism growth.

Other objects, advantages and features of the present invention will become apparent from the following specification taken in conjunction with the accompanying drawings.

BRIEF SUMMARY OF THE INVENTION

The present invention relates generally to peroxycarboxylic acid compositions, such as peroxyformic acid compositions, employing a self-indicating chemistry suitable for detecting efficacious levels of peroxycarboxylic acid concentrations in a solution in situ. Beneficially, the self-indicating chemistry compositions are non-destructive to the peroxycarboxylic acid compositions. In certain embodiments, the self-indicating chemistry compositions provide a stabilizing effect on the peroxycarboxylic acid concentrations. Methods of providing a visual indication of completion of a perhydrolysis reaction to generate a peroxycarboxylic acid composition employing a three dye system are provided. Methods of using the peroxycarboxylic acid compositions having a self-indicating chemistry for treating are target are further provided. An advantage of the invention is the visual assessment provided by a tri-color indicator system providing a user a clear basis to confirm a sufficient level of the peroxycarboxylic acid biocide has been produced in situ, and confirm when a peroxycarboxylic acid biocide concentration has decreased below a threshold concentration(s).

In an embodiment a self-indicating peroxycarboxylic acid chemistry composition comprises: a peroxycarboxylic acid; a background dye; and a latent peracid selective dye(s) which upon oxidation by the peroxycarboxylic acid provides a visual indication the presence of a minimum concentration of peroxycarboxylic acid for efficacy as an antimicrobial.

In an embodiment a method of generating a self-indicating peroxycarboxylic acid composition for surface disinfection comprises: contacting a first reagent with a second reagent, wherein the first reagent comprises at least one ester of a polyhydric alcohol and a C1-C18 carboxylic acid, and wherein the second reagent comprises hydrogen peroxide or a substance that generates hydrogen peroxide; generating a peroxycarboxylic acid in situ by perhydrolysis; and indicating a presence of a minimum concentration of the peroxycarboxylic acid through a non-fluorescent visual indicator comprising at least two dyes in the peroxycarboxylic acid, wherein the first reagent and said second reagent are kept separate prior to use.

In an embodiment a method of indicating the presence of a peroxycarboxylic acid concentration for surface disinfection comprises: generating a peroxycarboxylic acid in situ by perhydrolysis; contacting a latent dye of a visual indicator composition with a peroxycarboxylic acid to oxidize the latent dye; and indicating a presence of a desired concentration of the peroxycarboxylic acid for surface disinfection through the visual indicator composition comprising at least two dyes, wherein the combination of dyes have different half-lives to provide sustained visual indication of peroxycarboxylic acid concentration for at least 12 hours.

In an embodiment a kit comprises: a first reagent comprising at least one ester of a polyhydric alcohol and a C1-C18 carboxylic acid; a second reagent comprising hydrogen peroxide or a substance that generates hydrogen peroxide; and a non-fluorescent visual indicator comprising at least two dyes for providing a visual color indication correlated to a concentration of peroxycarboxylic acid, wherein the visual indicator can be a third reagent or combined with the first reagent; wherein combining the first reagent and the second reagent generates a peroxycarboxylic acid in situ by perhydrolysis reaction and the presence of the non-fluorescent visual indicator provides a color indication of the presence of a minimum concentration of the peroxycarboxylic acid for surface disinfection.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
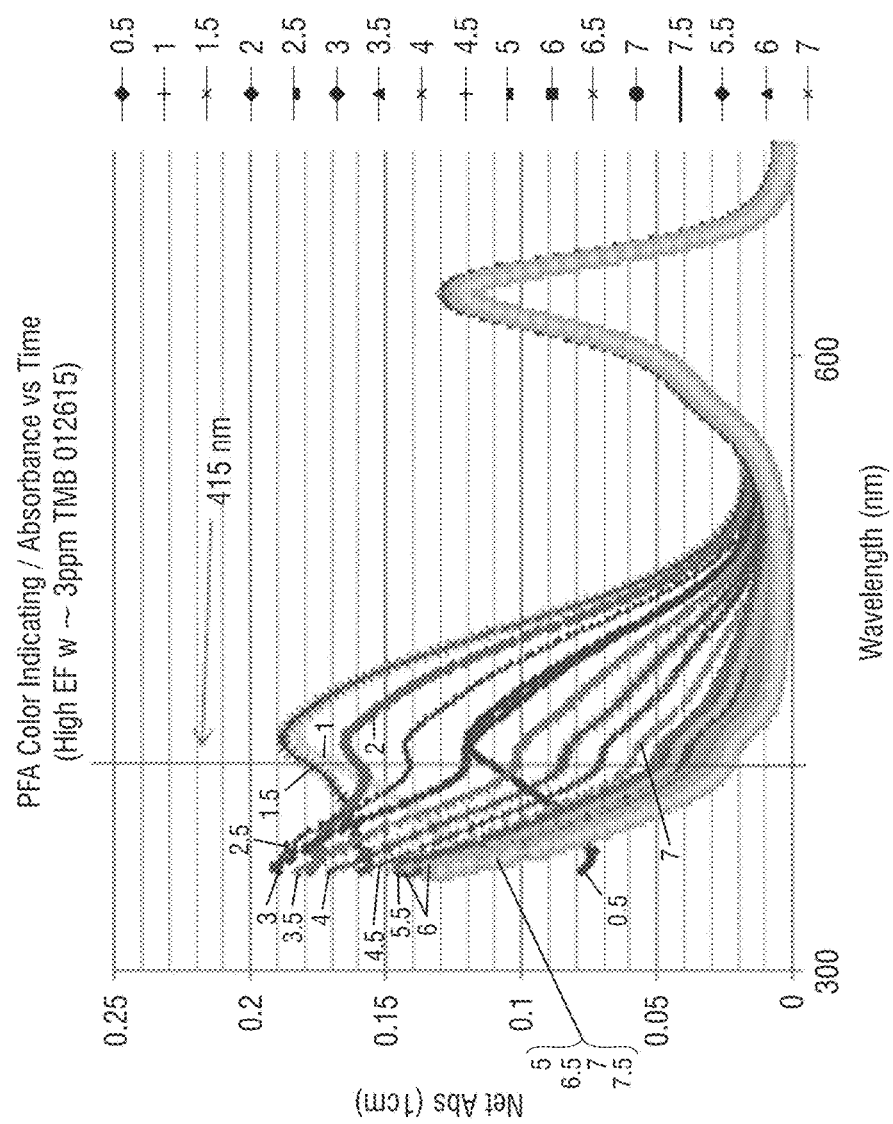
FIG. 1 shows a UV-VIS scan at 30 second intervals and respective absorptions depicting a performic acid visual indicator system according to embodiments of the invention.

The patent or application file contains at least one drawing executed in color. Copies of this patent or patent application publication with color drawing(s) will be provided by the Office upon request and payment of the necessary fee. Various embodiments of the present invention will be described in detail with reference to the drawings, wherein like reference numerals represent like parts throughout the several views. Reference to various embodiments does not limit the scope of the invention. Figures represented herein are not limitations to the various embodiments according to the invention and are presented for exemplary illustration of the invention.

DETAILED DESCRIPTION OF THE PREFERRED EMBODIMENT

The embodiments of this invention are not limited to particular peroxycarboxylic acid compositions or self-indicating chemistries for use with peroxycarboxylic acid compositions, which can vary and are understood by skilled artisans. It is further to be understood that all terminology used herein is for the purpose of describing particular embodiments only, and is not intended to be limiting in any manner or scope. For example, as used in this specification and the appended claims, the singular forms "a," "an" and "the" can include plural referents unless the content clearly indicates otherwise. Further, all units, prefixes, and symbols may be denoted in its SI accepted form.

Unless defined otherwise, all technical and scientific terms used herein have the same meaning as is commonly understood by one of ordinary skill in the art to which this invention belongs. All patents, applications, published applications and other publications referred to herein are incorporated by reference in their entireties. If a definition set forth in this section is contrary to or otherwise inconsistent with a definition set forth in the patents, applications, published applications and other publications that are herein incorporated by reference, the definition set forth in this section prevails over the definition that is incorporated herein by reference.

So that the present invention may be more readily understood, certain terms are first defined. Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments of the present invention without undue experimentation, the preferred materials and methods are described herein. In describing and claiming the embodiments of the present invention, the following terminology will be used in accordance with the definitions set out below.

Numeric ranges recited within the specification are inclusive of the numbers within the defined range. Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range (e.g. 1 to 5 includes 1, 1.5, 2, 2.75, 3, 3.80, 4, and 5).

The term "about," as used herein, refers to variation in the numerical quantity that can occur, for example, through typical measuring and liquid handling procedures used for making concentrates or use solutions in the real world; through inadvertent error in these procedures; through differences in the manufacture, source, or purity of the ingredients used to make the compositions or carry out the methods; and the like. The term "about" also encompasses amounts that differ due to different equilibrium conditions for a composition resulting from a particular initial mixture. Whether or not modified by the term "about", the claims include equivalents to the quantities.

The term "actives" or "percent actives" or "percent by weight actives" or "actives concentration" are used interchangeably herein and refers to the concentration of those ingredients involved in cleaning expressed as a percentage minus inert ingredients such as water or salts.

As used herein, the term "alkyl" or "alkyl groups" refers to saturated hydrocarbons having one or more carbon atoms, including straight-chain alkyl groups (e.g., methyl, ethyl, propyl, butyl, pentyl, hexyl, heptyl, octyl, nonyl, decyl, etc.), cyclic alkyl groups (or "cycloalkyl" or "alicyclic" or "carbocyclic" groups) (e.g., cyclopropyl, cyclopentyl, cyclohexyl, cycloheptyl, cyclooctyl, etc.), branched-chain alkyl groups (e.g., isopropyl, tert-butyl, sec-butyl, isobutyl, etc.), and alkyl-substituted alkyl groups (e.g., alkyl-substituted cycloalkyl groups and cycloalkyl-substituted alkyl groups).

Unless otherwise specified, the term "alkyl" includes both "unsubstituted alkyls" and "substituted alkyls." As used herein, the term "substituted alkyls" refers to alkyl groups having substituents replacing one or more hydrogens on one or more carbons of the hydrocarbon backbone. Such substituents may include, for example, alkenyl, alkynyl, halogeno, hydroxyl, alkylcarbonyloxy, arylcarbonyloxy, alkoxycarbonyloxy, aryloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), imino, sulfhydryl, alkylthio, arylthio, thiocarboxylate, sulfates, alkylsulfinyl, sulfonates, sulfamoyl, sulfonamido, nitro, trifluoromethyl, cyano, azido, heterocyclic, alkylaryl, or aromatic (including heteroaromatic) groups. In some embodiments, substituted alkyls can include a heterocyclic group. As used herein, the term "heterocyclic group" includes closed ring structures analogous to carbocyclic groups in which one or more of the carbon atoms in the ring is an element other than carbon, for example, nitrogen, sulfur or oxygen. Heterocyclic groups may be saturated or unsaturated. Exemplary heterocyclic groups include, but are not limited to, aziridine, ethylene oxide (epoxides, oxiranes), thiirane (episulfides), dioxirane, azetidine, oxetane, thietane, dioxetane, dithietane, dithiete, azolidine, pyrrolidine, pyrroline, oxolane, dihydrofuran, and furan.

The term "alkenyl" includes an unsaturated aliphatic hydrocarbon chain having from 2 to 12 carbon atoms, such as, for example, ethenyl, 1-propenyl, 2-propenyl. 1-butenyl, 2-methyl-1-propenyl, and the like. The alkyl or alkenyl can be terminally substituted with a heteroatom, such as, for example, a nitrogen, sulfur, or oxygen atom, forming an aminoalkyl, oxyalkyl, or thioalkyl, for example, aminomethyl, thioethyl, oxypropyl, and the like. Similarly, the above alkyl or alkenyl can be interrupted in the chain by a heteroatom forming an alkylaminoalky, 1, alkylthioalkyl, or alkoxyalkyl, for example, methylaminoethyl, ethylthiopropyl, methoxymethyl, and the like.

Further, as used herein the term "alicyclic" includes any cyclic hydrocarbyl containing from 3 to 8 carbon atoms. Examples of suitable alicyclic groups include cyclopropanyl, cyclobutanyl, cyclopentanyl, etc. The term "heterocyclic" includes any closed ring structures analogous to carbocyclic groups in which one or more of the carbon atoms in the ring is an element other than carbon (heteroatom), for example, a nitrogen, sulfur, or oxygen atom. Heterocyclic groups may be saturated or unsaturated. Examples of suitable heterocyclic groups include for example, aziridine, ethylene oxide (epoxides, oxiranes), thiirane (episulfides), dioxirane, azetidine, oxetane, thietane, dioxetane, dithietane, dithiete, azolidine, pyrrolidine, pyrroline, oxolane, dihydrofuran, and furan. Additional examples of suitable heterocyclic groups include groups derived from tetrahydrofurans, furans, thiophenes, pyrrolidines, piperidines, pyridines, pyrrols, picoline, coumaline, etc.

In some embodiments, alkyl, alkenyl, alicyclic groups, and heterocyclic groups can be unsubstituted or substituted by, for example, aryl, heteroaryl, $C_{1-4}$ alkyl, $C_{1-4}$ alkenyl, $C_{1-4}$ alkoxy, amino, carboxy, halo, nitro, cyano, —$SO_3H$, phosphono, or hydroxy. When alkyl, alkenyl, alicyclic group, or heterocyclic group is substituted, preferably the substitution is $C_{1-4}$ alkyl, halo, nitro, amido, hydroxy, carboxy, sulpho, or phosphono. In one embodiment, R includes alkyl substituted with hydroxy. The term "aryl" includes aromatic hydrocarbyl, including fused aromatic rings, such as, for example, phenyl and naphthyl. The term "heteroaryl" includes heterocyclic aromatic derivatives having at least one heteroatom such as, for example, nitrogen, oxygen, phosphorus, or sulfur, and includes, for example, furyl, pyrrolyl, thienyl, oxazolyl, pyridyl, imidazolyl, thiazolyl, isoxazolyl, pyrazolyl, isothiazolyl, etc. The term "heteroaryl" also includes fused rings in which at least one ring is aromatic, such as, for example, indolyl, purinyl, benzofuryl, etc.

In some embodiments, aryl and heteroaryl groups can be unsubstituted or substituted on the ring by, for example, aryl, heteroaryl, alkyl, alkenyl, alkoxy, amino, carboxy, halo, nitro, cyano, —$SO_3H$, phosphono, or hydroxy. When aryl, aralkyl, or heteroaryl is substituted, preferably the substitution is $C_{1-4}$ alkyl, halo, nitro, amido, hydroxy, carboxy, sulpho, or phosphono. In one embodiment, R includes aryl substituted with $C_{1-4}$ alkyl.

As used herein, the term "cleaning" refers to a method used to facilitate or aid in soil removal, bleaching, microbial population reduction, and any combination thereof. For the purpose of this patent application, successful microbial reduction is achieved when the microbial populations are reduced by at least about 50%, or by significantly more than is achieved by a wash with water. Larger reductions in microbial population provide greater levels of protection.

As used herein, the term "disinfectant" refers to an agent that kills all vegetative cells including most recognized pathogenic microorganisms, using the procedure described in *A.O.A.C. Use Dilution Methods*, Official Methods of Analysis of the Association of Official Analytical Chemists, paragraph 955.14 and applicable sections, 15th Edition, 1990 (EPA Guideline 91-2). As used herein, the term "high level disinfection" or "high level disinfectant" refers to a compound or composition that kills substantially all organisms, except high levels of bacterial spores, and is effected with a chemical germicide cleared for marketing as a sterilant by the Food and Drug Administration. As used herein, the term "intermediate-level disinfection" or "intermediate level disinfectant" refers to a compound or composition that kills mycobacteria, most viruses, and bacteria with a chemical germicide registered as a tuberculocide by the Environmental Protection Agency (EPA). As used herein, the term "low-level disinfection" or "low level disinfectant" refers to a compound or composition that kills some viruses and bacteria with a chemical germicide registered as a hospital disinfectant by the EPA.

As used herein, the term "free," "no," "substantially no" or "substantially free" refers to a composition, mixture, or ingredient that does not contain a particular compound or to which a particular compound or a particular compound-containing compound has not been added. In some embodiments, the reduction and/or elimination of hydrogen peroxide according to embodiments provide hydrogen peroxide-free or substantially-free compositions. Should the particular compound be present through contamination and/or use in a minimal amount of a composition, mixture, or ingredients, the amount of the compound shall be less than about 3 wt-%. More preferably, the amount of the compound is less than 2 wt-%, less than 1 wt-%, and most preferably the amount of the compound is less than 0.5 wt-%.

As used herein, the term "microorganism" refers to any noncellular or unicellular (including colonial) organism. Microorganisms include all prokaryotes. Microorganisms include bacteria (including cyanobacteria), spores, lichens, fungi, protozoa, virinos, viroids, viruses, phages, and some algae. As used herein, the term "microbe" is synonymous with microorganism.

As used herein, the terms "mixed" or "mixture" when used relating to "percarboxylic acid composition," "percarboxylic acids," "peroxycarboxylic acid composition" or "peroxycarboxylic acids" refer to a composition or mixture including more than one percarboxylic acid or peroxycarboxylic acid.

As used herein, the term "sanitizer" refers to an agent that reduces the number of bacterial contaminants to safe levels as judged by public health requirements. In an embodiment, sanitizers for use in this invention will provide at least a 3 log reduction and more preferably a 5-log order reduction. These reductions can be evaluated using a procedure set out in *Germicidal and Detergent Sanitizing Action of Disinfectants*, Official Methods of Analysis of the Association of Official Analytical Chemists, paragraph 960.09 and applicable sections, 15th Edition, 1990 (EPA Guideline 91-2). According to this reference a sanitizer should provide a 99.999% reduction (5-log order reduction) within 30 seconds at room temperature, 25±2° C., against several test organisms.

Differentiation of antimicrobial "-cidal" or "-static" activity, the definitions which describe the degree of efficacy, and the official laboratory protocols for measuring this efficacy are considerations for understanding the relevance of antimicrobial agents and compositions. Antimicrobial compositions can affect two kinds of microbial cell damage. The first is a lethal, irreversible action resulting in complete microbial cell destruction or incapacitation. The second type of cell damage is reversible, such that if the organism is rendered free of the agent, it can again multiply. The former is termed microbiocidal and the later, microbistatic. A sanitizer and a disinfectant are, by definition, agents which provide antimicrobial or microbiocidal activity. In contrast, a preservative is generally described as an inhibitor or microbistatic composition The term "substantially similar cleaning performance" refers generally to achievement by a substitute cleaning product or substitute cleaning system of generally the same degree (or at least not a significantly lesser degree) of cleanliness or with generally the same expenditure (or at least not a significantly lesser expenditure) of effort, or both.

As used herein, the term "sulfoperoxycarboxylic acid," "sulfonated peracid," or "sulfonated peroxycarboxylic acid" refers to the peroxycarboxylic acid form of a sulfonated carboxylic acid. In some embodiments, the sulfonated peracids of the present invention are mid-chain sulfonated peracids. As used herein, the term "mid-chain sulfonated peracid" refers to a peracid compound that includes a sulfonate group attached to a carbon that is at least one carbon (e.g., the three position or further) from the carbon of the percarboxylic acid group in the carbon backbone of the percarboxylic acid chain, wherein the at least one carbon is not in the terminal position. As used herein, the term "terminal position," refers to the carbon on the carbon backbone chain of a percarboxylic acid that is furthest from the percarboxyl group.

As used herein, the term "waters" includes food process or transport waters. Food process or transport waters include produce transport waters (e.g., as found in flumes, pipe transports, cutters, slicers, blanchers, retort systems, washers, and the like), belt sprays for food transport lines, boot and hand-wash dip-pans, third-sink rinse waters, and the like. Waters also include domestic and recreational waters such as pools, spas, recreational flumes and water slides, fountains, and the like.

The term "weight percent," "wt-%," "percent by weight," "% by weight," and variations thereof, as used herein, refer to the concentration of a substance as the weight of that substance divided by the total weight of the composition and multiplied by 100. It is understood that, as used here, "percent." "%," and the like are intended to be synonymous with "weight percent," "wt-%," etc.

The methods, systems, and compositions of the present invention may comprise, consist essentially of, or consist of the components and ingredients of the present invention as well as other ingredients described herein. As used herein, "consisting essentially of" means that the methods, systems, and compositions may include additional steps, components or ingredients, but only if the additional steps, components or ingredients do not materially alter the basic and novel characteristics of the claimed methods, systems, and compositions.

Compositions

The compositions and methods employing the compositions according to the invention include a self-indicating chemistry composition suitable for use with a peroxycarboxylic acid composition. In an aspect, the self-indicating chemistry composition comprises a combination of three dyes, and the peroxycarboxylic acid forming composition comprises at least two reagents, wherein a first reagent comprises an ester of a polyhydric alcohol and a carboxylic acid, and wherein a second reagent comprises hydrogen peroxide or a hydrogen peroxide source. In an aspect, the self-indicating chemistry composition is combined with the first reagent. In a further aspect, the self-indicating chemistry and the first reagent are combined with the second reagent to generate a desired peroxycarboxylic acid in the presence of the self-indicating chemistry compositions to provide visual indicators to a user of the concentrations of the peroxycarboxylic acid.

Self-Indicating Chemistry Compositions

In an aspect, the self-indicating chemistry compositions comprise a combination of at least two dyes. In a further aspect, the self-indicating chemistry compositions comprise a combination of three dyes. In a further aspect, the combination of dyes provides a visual indication system suitable for detecting the formation or generation of a peroxycarboxylic acid formed in a perhydrolysis reaction. Preferably, the combination of dyes provides a visual indication system using three distinct colors (e.g. blue, green, yellow). In an aspect, the combination of dyes provides a non-fluorescent visual indicator for the peroxycarboxylic acid compositions. In a further aspect, the combination of dyes are non-staining to a treated system.

Suitable dyes for use in the self-indicating chemistry composition include oxidize able dyes, including those insensitive to hydrogen peroxide driving a perhydrolysis reaction to generate a peroxycarboxylic acid composition. In an aspect, the self-indicating chemistry composition include a combination of dyes having different half-lives in order to provide sustained visual indicators, such as for up to 7 days, or from 1 to 7 days, or from 12 hours to 7 days. In an aspect, the self-indicating chemistry composition include a combination of HRP substrates and synthetic dyes. In an aspect, the HRP substrates provide a long half-life and as the latent chromophore which does not result in a color (e.g. green) until oxidation the self-indicating chemistry composition is able to retain a visual indicator of the presence of the peroxycarboxylic acid concentration for up to 7 days, or from 1 to 7 days, or from 12 hours to 7 days due to the half-life of the HRP substrate. Exemplary half-lives for the exemplary dyes employed in the self-indicating chemistry compositions are shown below in Examples.

Latent Peracid Selective Dyes and HRP Substrates

In an aspect, the self-indicating chemistry composition includes at least one latent peracid selective dyes. In a further aspect, the latent peracid selective dye is a peroxide sensitive dye. In a further aspect, the latent peracid selective dye is a horse radish peroxidase enzyme (HRP) substrate. In a further aspect, the latent peracid selective dye is a peroxide and horse radish peroxidase enzyme (HRP) substrate to provide a yellow visual indicator. In an aspect, the yellow visual indicator is a latent dye which is selective for peroxycarboxylic acids. Suitable commercially-available latent peracid selective dyes (and HRP substrates) include PNPP (p-Nitrophenyl Phosphate, Disodium Salt), ABTS (2,2'-Azinobis [3-ethylbenzothiazoline-6-sulfonic acid]-diammonium salt) CAS 30931-67-0, OPD (o-phenylenediamine dihydrochloride), and TMB (3,3',5,5'-tetramethylbenzidine) CAS 54827-17-7.

Additional latent peracid selective dyes suitable for use according to the invention include latent chromophores which have been shown to be sensitive to oxidation by hydrogen peroxide in the presence of HRP and which presumably will show peracid sensitivity, including the following:

Amplex Red (Resazurin) 7-hydroxy-10-oxidophenox-azin-10-ium-3-one;

Homovanillic acid (3-methoxy-4-hydroxyphenyl acetic acid);

AEC (3-amino-9-ethylcarbazole);

DAB (Diaminobenzidine); and

Compounds depicted in the following formulas:

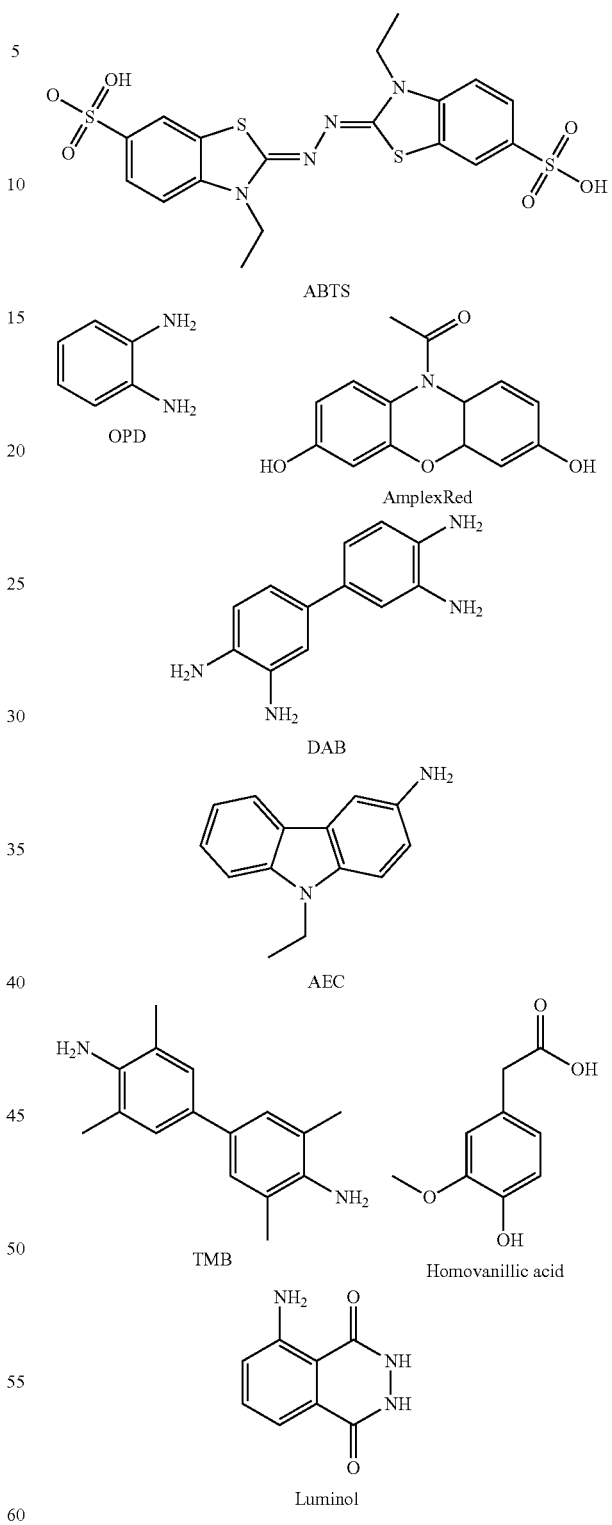

In some aspects it is desirable to employ a combination of dyes having different light absorbance, yielding different colors and/or different rates of color generation. In an aspect, it is desirable to have a first HRP substrate yielding a color within a matter of seconds and a second HRP substrate yielding a color within a matter of minutes. For example:

PNPP produces a yellow water-soluble reaction product that absorbs light at 405 nm; ABTS (2,2'-Azinobis [3-ethylbenzothiazoline-6-sulfonic acid]-diammonium salt) produces a green water-soluble reaction product that has two major absorbance peaks at 410 nm and 650 nm and provides slow color development; OPD (o-phenylenediamine dihydrochloride) produces a yellow-orange water soluble reaction product with an absorbance maximum of 492 nm; and TMB (3,3',5,5'-tetramethylbenzidine) yields a soluble blue color and has an absorbance maxima or the reaction product are 370 nm and 652 nm, wherein the color then changes to yellow with the addition of sulfuric or phosphoric acid with maximum absorbance at 450 nm.

In an aspect, self-indicating chemistry composition includes at least one HRP substrate selected from the group consisting of PNPP (p-Nitrophenyl Phosphate, Disodium Salt), ABTS (2,2'-Azinobis [3-ethylbenzothiazoline-6-sulfonic acid]-diammonium salt), OPD (o-phenylenediamine dihydrochloride), TMB (3,3',5,5'-tetramethylbenzidine), and combinations thereof. In a further aspect, self-indicating chemistry composition includes at least two HRP substrates selected from the group consisting of PNPP (p-Nitrophenyl Phosphate, Disodium Salt), ABTS (2,2'-Azinobis [3-ethylbenzothiazoline-6-sulfonic acid]-diammonium salt), OPD (o-phenylenediamine dihydrochloride), TMB tetramethylbenzidine), and combinations thereof.

In an aspect, the self-indicating chemistry compositions include two latent peracid selective dyes having a ratio of from about 1:5 to 5:1, from about 1:3 to 3:1, or from about 1:2 to 2:1.

In an aspect, the self-indicating chemistry compositions include two latent peracid selective dyes having a ratio of about 1:3 to 3:1, or preferably 2:3 to 3:2, and more preferably about 2:3 (TMB:ABTS) which beneficially provides a near optimum generation of an intense yellow visual indivator (via TMB) and is removed by bleaching of the ABTS to provide the sustained oxidized dye according to the invention.

In an aspect, the self-indicating chemistry compositions include from about 0.0001 wt-%-5 wt-% of one or more latent peracid selective dyes, from about 0.0001 wt-%-0.001 wt-% of one or more latent peracid selective dyes, or preferably from about 0.0001 wt-%-0.1 wt-% of one or more latent peracid selective dyes. In addition, without being limited according to the invention, all ranges recited are inclusive of the numbers defining the range and include each integer within the defined range.

Background Dye

In an aspect, the self-indicating chemistry composition include at least background dye to provide a green visual indicator. As referred to herein, background dyes are produced using aromatic hydrocarbons from petroleum. Exemplary and non-limiting suitable commercially-available background dyes include FD&C Blue No. 1 having the formula $C_{37}H_{34}N_2Na_2O_9S_3$ (ethyl-[4-[[4-[ethyl-[(3-sulfophenyl) methyl]amino] phenyl]-(2-sulfophenyl) methylidene]-1-cyclohexa-2, 5-dienylidene]-[(3-sulfophenyl) methyl] azanium), Acid Blue 9, D&C Blue No. 4, Atracid Blue FG, Erioglaucine, Eriosky blue, Patent Blue AR, Xylene Blue VSG, and the like.

A background dye may be selected based upon desired characteristic of its half-life to correlate a visual indicator with the concentrations of a peroxycarboxylic acid composition in the self-indicating chemistry composition.

In an aspect, the background dye may be visible at time zero and thereafter fade in the self-indicating peracid chemistry composition. In another aspect, the background dye resists fading or bleaching.

In an aspect, the self-indicating chemistry compositions include a background dye in addition to the latent peracid selective dyes, wherein the ratio of the latent peracid selective dyes to the background dye is from about 20:1 to 1:1, from about 15:1 to 1:1, from about 15:1 to 5:1, from about 15:1 to 10:1, or about 10:1.

In an aspect, the self-indicating chemistry composition include from about 0.001 wt-%-1 wt-% of one or more synthetic dyes, from about 0.005 wt-%-0.5 wt-% of one or more synthetic dyes, from about 0.01 wt-%-0.5 wt-% of one or more synthetic dyes, preferably from about 0.01 wt-%-0.1 wt-% of one or more synthetic dyes. In addition, without being limited according to the invention, all ranges recited are inclusive of the numbers defining the range and include each integer within the defined range.

Peroxycarboxylic Acid Forming Compositions

The present invention relates to peroxycarboxylic acid forming compositions suitable for use with self-indicating chemistry compositions and uses thereof. In one aspect, the present invention is directed to a peroxycarboxylic acid forming composition comprising: a first reagent that comprises an ester of a polyhydric alcohol and a carboxylic acid, and a second reagent that comprises hydrogen peroxide or that comprises a substance that generates hydrogen peroxide when in contact with a liquid. In a further aspect, the first reagent further comprises the self-indicating chemistry composition. In a further aspect, the first reagent and second reagent are kept separately prior to use and combined when it is time to generate the peroxycarboxylic acid.

In an aspect, the first reagent is provided in amount from about 1% to about 10%, preferably from about 2% to about 5%. In an aspect, the second reagent is provided in amount from about 90% to about 99%, preferably from about 95% to about 98%.

Table 1 shows exemplary ranges of the total weight-percentage of the components for use in the combined amounts of the first and second reagents according to the peroxycarboxylic acid forming compositions of the invention.

TABLE 1

|  | First Exemplary Embodiment | Second Exemplary Embodiment | Third Exemplary Embodiment |
| --- | --- | --- | --- |
| Ester of Polyhydric Alcohol and Carboxylic Acid | 0.1-50% | 0.5-20% | 1-10% |
| Hydrogen Peroxide | 0.1-50% | 0.5-20% | 1-10% |
| Self-Indicating Chemistry Composition | 0.0001-5% | 0.0001-0.1000% | 0.0001-0.001% |

TABLE 1-continued

| | First Exemplary Embodiment | Second Exemplary Embodiment | Third Exemplary Embodiment |
|---|---|---|---|
| Additional Functional Ingredients (e.g. acidulant, stabilizers, buffers) | 0.01-10 | 0.1-1 | 0.0001-0.2% |

In a still further aspect, the first reagent and second reagent are configured to be contacted with each other to form a liquid that comprises a peroxycarboxylic acid and has a pH ranging from about 0 to about 11, and pH of the formed liquid becomes about 8 or lower within about 1 minute after the contact between said first reagent and said second reagent. In an alternative aspect, the second reagent comprises a substance that generates hydrogen peroxide when in contact with a liquid, the first reagent and second reagent are comprised in a solid composition, and when it is time to generate the peroxycarboxylic acid, the solid composition is configured to be contacted with a liquid to form a liquid that comprises the peroxycarboxylic acid and has a pH ranging from about 0 to about 11, and pH of the formed liquid becomes about 8 or lower within about 1 minute after the contact between said solid composition and said liquid.

Esters of polyhydric alcohols and a C1-C18 carboxylic acid are included in the first reagent. A polyhydric alcohol refers to an molecule with two or more hydroxyl (—OH) groups. An ester of a polyhydric alcohol and a carboxylic acid refers to an ester formed between a polyhydric alcohol and the carboxylic acid. A variety of carboxylic acids can be included. Carboxylic acids generally have the formula R(COOH)n, where, for example, R is an alkyl, aryl alkyl, cycloalkyl, aromatic, or heterocyclic group, and n is one, two, or three.

In an embodiment the polyhydric alcohol may include a sugar alcohol. In an embodiment where the peroxycarboxylic acid is peroxyformic, the first reagent may comprise glycerol formates, pentaerythritol formats, mannitol formats, propylene glycol formates, sorbitol formates and sugar formates. In such an exemplary embodiment, any suitable sugar formats may be employed, e.g., sucrose formates, dextrin formates, maltodextrin formates, or starch formates.

The compositions can also include more than one or a mixture of esters of a polyhydric alcohol and a carboxylic acid. For example, in some embodiments, the compositions include two, three or four esters. When more than one ester is present, the esters can be different. For example, in some embodiments, the compositions can include a first ester of a polyhydric alcohol and a C1 to C4 carboxylic acid, and a second ester of a polyhydric alcohol and a C5 to C11 carboxylic acid. For further example, in some embodiments, the compositions can include a first ester of a polyhydric alcohol and a C1 to C18 carboxylic acid in a mono, di or tri-formation, and a second ester of a polyhydric alcohol and a C1 to C18 carboxylic acid in a mono, di or tri-formation. One skilled in the art will appreciate the various combinations of esters that can be used for the compositions according to the invention.

The use of various forms of an ester (e.g. mono, di and/or tri-formations) to comprise a mixture of esters will impact the peracid yield of a particular composition according to the invention. For example, the various forms of the ester will have different kinetics in generating the peracids according to the methods of the invention. For example, in one aspect, a monooctanoate glycerol ester is faster in generating peracid than the di- or trioctanoate glycerol esters. In addition, the selection of the various forms of an ester will be further impacted by the water solubility of the compositions and whether any additional ingredients are combined to affect solubility (e.g. solvents) that would favor the use of less soluble ester forms (e.g. tri-formations). Accordingly, one skilled in the art of reaction kinetics will ascertain the benefits of using various combinations or mixtures of esters according to the compositions and methods of the invention.

Examples of suitable carboxylic acids include, but are not limited to, formic, acetic, propionic, butanoic, pentanoic, hexanoic, heptanoic, octanoic, nonanoic, decanoic, undecanoic, dodecanoic, as well as their branched isomers, lactic, maleic, ascorbic, citric, hydroxy acetic, neopentanoic, neoheptanoic, neodecanoic, oxalic, malonic, succinic, glutaric, adipic, pimelic subric acid, and mixtures thereof.

The peroxycarboxylic acid forming compositions can comprise any suitable level of an ester of a polyhydric alcohol and carboxylic acid (including either liquid or solid reagents). For example, the first reagent of the peroxycarboxylic acid forming composition can comprise any suitable level of an ester of a polyhydric alcohol and carboxylic acid. In some embodiments, the first reagent can comprise from about 10 ppm to about 500,000 ppm of an ester of a polyhydric alcohol and carboxylic acid. For example, the first reagent can comprise from about 10-20 ppm, 20-30 ppm, 30-40 ppm, 40-50 ppm, 50-60 ppm, 60-70 ppm, 70-80 ppm, 80-90 ppm, 90-100 ppm, 100-150 ppm, 150-200 ppm, 200-250 ppm, 250-300 ppm, 300-350 ppm, 350-400 ppm, 400-450 ppm, 450-500 ppm, 500-550 ppm, 550-600 ppm, 600-650 ppm, 650-700 ppm, 700-750 ppm, 750-800 ppm, 800-850 ppm, 850-900 ppm, 900-950 ppm, 950-1,000 ppm, 1,000-1,500 ppm, 1,500-2,000 ppm, 2,000-2,500 ppm, 2,500-3,000 ppm, 3,000-3,500 ppm, 3,500-4,000 ppm, 4,000-4,500 ppm, 4,500-5,000 ppm, 5,000-5,500 ppm, 5,500-6,000 ppm, 6,000-6,500 ppm, 6,500-7,000 ppm, 7,000-7,500 ppm, 7,500-8,000 ppm, 8,000-8,500 ppm, 8,500-9,000 ppm, 9,000-10,000 ppm, 10,000-20,000 ppm, 20,000-30,000 ppm, 30,000-40,000 ppm, 40,000-50,000 ppm, 50,000-60,000 ppm, 60,000-70,000 ppm, 70,000-80,000 ppm, 80,000-90,000 ppm, 90,000-100,000 ppm, 100,000-150,000 ppm, 150,000-200,000 ppm, 200,000-250,000 ppm, 250,000-300,000 ppm, 300,000-350,000 ppm, 350,000-400,000 ppm, 400,000-450,000 ppm, or 450,000-500,000 ppm. In other embodiments, the first reagent can comprise from about 50 ppm to about 40,000 ppm of an ester of a polyhydric alcohol and carboxylic acid, e.g., 50-100, 50-500, 50-1,000, 50-1,500, 50-2,000, 50-2,500, 50-3,000, 50-3,500, 50-4,000, 50-4,500, 50-5,000, 50-10,000, 50-20,000, 50-30,000, or 50-40,000 ppm of an ester of a polyhydric alcohol and carboxylic acid.

Hydrogen peroxide (or a source of hydrogen peroxide, such as a substance that generates hydrogen peroxide upon contact with a liquid) is employed in the second reagent. The peroxycarboxylic acid forming compositions can comprise any suitable level of hydrogen peroxide or a substance that generates hydrogen peroxide upon contact with a liquid. For example, the second reagent of the peroxycarboxylic acid forming composition can comprise any suitable level of hydrogen peroxide or a source of hydrogen peroxide. In some embodiments, the second reagent can comprise about 1 ppm to about 300,000 ppm of hydrogen peroxide or a source of hydrogen peroxide. For example, the second reagent can comprise from about 1-10 ppm, 10-20 ppm, 20-30 ppm, 30-40 ppm, 40-50 ppm, 50-60 ppm, 60-70 ppm, 70-80 ppm, 80-90 ppm, 90-100 ppm, 100-150 ppm, 150-200 ppm, 200-250 ppm, 250-300 ppm, 300-350 ppm, 350-400 ppm, 400-450 ppm, 450-500 ppm, 500-550 ppm, 550-600 ppm, 600-650 ppm, 650-700 ppm, 700-750 ppm, 750-800 ppm, 800-850 ppm, 850-900 ppm, 900-950 ppm, 950-1,000 ppm, 1,000-1,500 ppm, 1,500-2,000 ppm, 2,000-2,500 ppm, 2,500-3,000 ppm, 3,000-3,500 ppm, 3,500-4,000 ppm, 4,000-4,500 ppm, 4,500-5,000 ppm, 5,000-5,500 ppm, 5,500-6,000 ppm, 6,000-6,500 ppm, 6,500-7,000 ppm, 7,000-7,500 ppm, 7,500-8,000 ppm, 8,000-8,500 ppm, 8,500-9,000 ppm, 9,000-10,000 ppm, 10,000-20,000 ppm, 20,000-30,000 ppm, 30,000-40,000 ppm, 40,000-50,000 ppm, 50,000-60,000 ppm, 60,000-70,000 ppm, 70,000-80,000 ppm, 80,000-90,000 ppm, or 90,000-100,000 ppm, 100,000-150,000 ppm, 150,000-200,000 ppm, 200,000-250,000 ppm, or 250,000-300,000 ppm hydrogen peroxide or a source of hydrogen peroxide. In other embodiments, the second reagent comprises from about 150 ppm to about 50,000 ppm of hydrogen peroxide or a source of hydrogen peroxide, e.g., about 150-200, 150-300, 150-400, 150-500, 150-600, 150-700, 150-800, 150-900, 150-1,000, 150-1,500, 150-2,000, 150-2,500, 150-3,000, 150-3,500, 150-4,000, 150-4,500, 150-5,000, 150-10,000, 50-20,000, 50-30,000, 50-40,000 or 50-50,000 ppm of hydrogen peroxide or a source of hydrogen peroxide.

The peroxycarboxylic acid forming compositions can include any C1-C18 peroxycarboxylic acid, including mixtures of peroxycarboxylic acids, including for example, peroxyformic acid, peroxyacetic acid, peroxyoctanoic acid and/or peroxysulfonated oleic acid. As used herein, the term "peracid" may also be referred to as a "percarboxylic acid," "peroxycarboxylic acid" or "peroxyacid." Sulfoperoxycarboxylic acids, sulfonated peracids and sulfonated peroxycarboxylic acids are also included within the terms "peroxycarboxylic acid" and "peracid" as used herein. The terms "sulfoperoxycarboxylic acid," "sulfonated peracid," or "sulfonated peroxycarboxylic acid" refers to the peroxycarboxylic acid form of a sulfonated carboxylic acid as disclosed in U.S. Pat. No. 8,344,026, and U.S. Patent Publication Nos. 2010/0048730 and 2012/0052134, each of which are incorporated herein by reference in their entirety. As one of skill in the art appreciates, a peracid refers to an acid having the hydrogen of the hydroxyl group in carboxylic acid replaced by a hydroxy group. Oxidizing peracids may also be referred to herein as peroxycarboxylic acids.

A peracid includes any compound of the formula R—(COOOH)n in which R can be hydrogen, alkyl, alkenyl, alkyne, acylic, alicyclic group, aryl, heteroaryl, or heterocyclic group, and n is 1, 2, or 3, and named by prefixing the parent acid with peroxy. Preferably R includes hydrogen, alkyl, or alkenyl. The terms "alkyl," "alkenyl," "alkyne," "acylic," "alicyclic group," "aryl," "heteroaryl," and "heterocyclic group" are as defined herein. A sulfoperoxycarboxylic acid has the following formula:

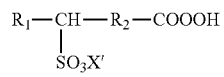

wherein $R_1$ is hydrogen, or a substituted or unsubstituted alkyl group; $R_2$ is a substituted or unsubstituted alkylene group; X is hydrogen, a cationic group, or an ester forming moiety; or salts or esters thereof. In additional embodiments, a sulfoperoxycarboxylic acid is combined with a single or mixed peroxycarboxylic acid composition, such as a sulfoperoxycarboxylic acid with peroxyacetic acid and peroxyoctanoic acid (PSOA/POOA/POAA).

In some embodiments, a mixed peracid is employed, such as a peroxycarboxylic acid including at least one peroxycarboxylic acid of limited water solubility in which R includes alkyl of 5-18 carbon atoms and at least one water-soluble peroxycarboxylic acid in which R includes alkyl of 1-4 carbon atoms. For example, in one embodiment, a peroxycarboxylic acid includes peroxyacetic acid and at least one other peroxycarboxylic acid such as those named above. Preferably a composition of the invention includes peroxyformic acid, peroxyacetic acid and/or peroxyoctanoic acid. Other combinations of mixed peracids are well suited for use in the current invention. Advantageously, a combination of peroxycarboxylic acids provides a composition with desirable antimicrobial activity in the presence of high organic soil loads. The mixed peroxycarboxylic acid compositions often provide synergistic micro efficacy. Accordingly, compositions of the invention can include a peroxycarboxylic acid, or mixtures thereof.

The first or second reagent and the generated liquid peroxycarboxylic acid composition can have any suitable pH range. For example, the first or second reagent and the generated liquid peroxycarboxylic acid composition can have a pH ranging from about 0 to about 11, e.g., about 0-1, 0-2, 0-3, 0-4, 0-5, 0-6, 0-7, 0-8, 0-9, 0-10, 0-11, 1-2, 1-3, 1-4, 1-5, 1-6, 1-7, 1-8, 1-9, 1-10, 1-11, 2-3, 2-4, 2-5, 2-6, 2-7, 2-8, 2-9, 2-10, 2-11, 3-4, 3-5, 3-6, 3-7, 3-8, 3-9, 3-10, 3-11, 4-5, 4-6, 4-7, 4-8, 4-9, 4-10, 4-11, 5-6, 5-7, 5-8, 5-9, 5-10, 5-11, 6-7, 6-8, 6-9, 6-10, 6-11, 6-7, 7-8, 7-9, 7-10, 7-11, 8-9, 8-10, 8-11, 9-10, 9-11, 10-11, or at about 0, 1, 2, 3, 4, 5, 6, 7, 8, 9, 10 or 11. In some embodiments, the first or second reagent and the generated liquid peroxycarboxylic acid composition has a pH ranging from about 5 to about 10, e.g., about 5-6, 5-7, 5-8, 5-9, 5-10, 6-7, 6-8, 6-9, 6-10, 7-8, 7-9, 7-10, 8-9, 8-10, or 9-10. In other embodiments, the first or second reagent has a pH at about 9. In other embodiments, the first reagent and the second reagent are configured to be contacted with each other to form a liquid peroxycarboxylic acid and has a pH at about 9.

The first reagent and the second reagent can be configured to be contacted with each other to form a liquid peroxycarboxylic acid under any suitable conditions or temperature. In some embodiments, the first reagent and the second reagent are configured to be contacted with each other under ambient conditions. In other embodiments, the first reagent and the second reagent are configured to be contacted with each at a temperature ranging from about 4° C. to about 60° C., e.g., about 4° C.-5° C., 5° C.-10° C., 10° C.-15° C., 15° C.-20° C., 20° C.-25° C., 25° C.-30° C., 30° C.-35° C., 35° C.-40° C., 40° C.-45° C., 45° C.-50° C., 50° C.-55° C., or 55° C.-60° C. In still other embodiments, the first reagent and the second reagent are configured to be contacted with each other to form a liquid peroxycarboxylic acid at a temperature at about 4° C. or lower than 4° C., e.g., at about 3° C., 2° C., 1° C., 0° C., or lower than 0° C.

The peroxycarboxylic acid forming compositions can be configured to form a liquid, e.g., a solution, that comprises any suitable level of the peroxycarboxylic acid. For example, the first reagent and the second reagent in the peroxycarboxylic acid forming compositions can be configured to be contacted with each other to form a liquid and/or solid, e.g., a solution, that comprises any suitable level of the peroxycarboxylic acid. In some embodiments, the first reagent and the second reagent can be configured to be contacted with each other to form a liquid, e.g., a solution, that comprises from about 0.1 ppm to about 5,000 ppm of peroxycarboxylic acid, e.g., about 0.1-1 ppm, 1-10 ppm, 10-20 ppm, 20-30 ppm, 30-40 ppm, 40-50 ppm, 50-60 ppm, 60-70 ppm, 70-80 ppm, 80-90 ppm, 90-100 ppm, 100-150 ppm, 150-200 ppm, 200-250 ppm, 250-300 ppm, 300-350 ppm, 350-400 ppm, 400-450 ppm, 450-500 ppm, 500-550 ppm, 550-600 ppm, 600-650 ppm, 650-700 ppm, 700-750 ppm, 750-800 ppm, 800-850 ppm, 850-900 ppm, 900-950 ppm, 950-1,000 ppm, 1,000-1,500 ppm, 1,500-2,000 ppm, 2,000-2,500 ppm, 2,500-3,000 ppm, 3,000-3,500 ppm, 3,500-4,000 ppm, 4,000-4,500 ppm, or 4,500-5,000 ppm of peroxycarboxylic acid.

In other embodiments, the first reagent and the second reagent can be configured to be contacted with each other to form a liquid, e.g., a solution, that comprises from about 1 ppm to about 500 ppm of peroxycarboxylic acid, e.g., about 0.1-1 ppm, 0.1-10 ppm, 0.1-20 ppm, 0.1-30 ppm, 0.1-40 ppm, 0.1-50 ppm, 0.1-60 ppm, 0.1-70 ppm, 0.1-80 ppm, 0.1-90 ppm, 0.1-100 ppm, 0.1-150 ppm, 0.1-200 ppm, 0.1-250 ppm, 0.1-300 ppm, 0.1-350 ppm, 0.1-400 ppm, 0.1-450 ppm, 0.1-500 ppm of peroxycarboxylic acid. In still other embodiments, the first reagent and the second reagent can be configured to be contacted with each other to form a liquid, e.g., a solution, that comprises from about 50 ppm to about 100 ppm of peroxycarboxylic acid, e.g., about 50-60 ppm, 60-70 ppm, 70-80 ppm, 80-90 ppm or 90-100 ppm of peroxycarboxylic acid.

In another example, the solid composition can be configured to be contacted with a liquid to form a solution that comprises from about 0.1 ppm to about 5,000 ppm of peroxycarboxylic acid. In some embodiments, the solid composition can be configured to be contacted with a liquid to form a liquid, e.g., a solution, that comprises from about 0.1 ppm to about 5,000 ppm of peroxycarboxylic acid, e.g., about 0.1-1 ppm, 1-10 ppm, 10-20 ppm, 20-30 ppm, 30-40 ppm, 40-50 ppm, 50-60 ppm, 60-70 ppm, 70-80 ppm, 80-90 ppm, 90-100 ppm, 100-150 ppm, 150-200 ppm, 200-250 ppm, 250-300 ppm, 300-350 ppm, 350-400 ppm, 400-450 ppm, 450-500 ppm, 500-550 ppm, 550-600 ppm, 600-650 ppm, 650-700 ppm, 700-750 ppm, 750-800 ppm, 800-850 ppm, 850-900 ppm, 900-950 ppm, 950-1,000 ppm, 1,000-1,500 ppm, 1,500-2,000 ppm, 2,000-2,500 ppm, 2,500-3,000 ppm, 3,000-3,500 ppm, 3,500-4,000 ppm, 4,000-4,500 ppm, or 4,500-5,000 ppm of peroxycarboxylic acid.

The peroxycarboxylic acid forming compositions (liquids or solids) can be configured to form the resultant compositions comprising any suitable level of peroxycarboxylic acid within any suitable time. In some embodiments, the first reagent and the second reagent can be configured to be contacted with each other to form the peroxycarboxylic acid composition that comprises at least about 1 ppm peroxycarboxylic acid within 1 minute of the contact time, e.g., at least about 1 ppm, 2 ppm, 3 ppm, 4 ppm, 5 ppm, 6 ppm, 7 ppm, 8 ppm, 9 ppm, 10 ppm, 15 ppm, 20 ppm, 25 ppm, 30 ppm, 35 ppm, 40 ppm, 45 ppm, 50 ppm, 55 ppm, 60 ppm, 65 ppm, 70 ppm, 75 ppm, 80 ppm, 85 ppm, 90 ppm, 95 ppm, 100 ppm, 200 ppm, 300 ppm, 400 ppm, 500 ppm, 600 ppm, 700 ppm, 800 ppm, 900 ppm, 1,000 ppm, 2,000 ppm, 3,000 ppm, 4,000 ppm, or 5,000 ppm of peroxycarboxylic acid within 1 minute, within 5 minutes, within 10 minutes, or greater of the contact time.

Exemplary Embodiments of Peroxycarboxylic Acid Forming Compositions

In a preferred embodiment for forming a peroxyformic acid composition, the first reagent comprises an ester of a polyhydric alcohol and formic acid, and the second reagent that comprises hydrogen peroxide or that comprises a substance that generates hydrogen peroxide when in contact with a liquid, wherein said first reagent and said second reagent are kept separately prior to use, and when it is time to generate peroxyformic acid, said first reagent and said second reagent are configured to be contacted with each other to form a liquid that comprises peroxyformic acid and has a pH ranging from about 0 to about 11, and pH of the formed liquid becomes about 8 or lower within about 1 minute after the contact between said first reagent and said second reagent. In other embodiments, the present peroxyformic acid forming composition comprises a first reagent that comprises an ester of a polyhydric alcohol and formic acid, and a second reagent that comprises a substance that generates hydrogen peroxide when in contact with a liquid, wherein said first reagent and said second reagent are comprised in a solid composition, and when it is time to generate peroxyformic acid, said solid composition is configured to be contacted with a liquid to form a liquid that comprises peroxyformic acid and has a pH ranging from about 0 to about 11, and pH of the formed liquid becomes about 8 or lower within about 1 minute after the contact between said solid composition and said liquid.

In a preferred embodiment for forming a peroxyformic acid composition the pH of the formed liquid can become about 8 or lower within about 1 minute after the contact between the first reagent and the second reagent or after the contact between the solid composition and the liquid. In some embodiments, the pH of the formed liquid can become about 8 or lower within about 1 second, 2 seconds, 3 seconds, 4 seconds, 5 seconds, 6 seconds, 7 seconds, 8 seconds, 9 seconds, 10 seconds, 20 seconds, 30 seconds, 40 seconds, 50 seconds after the contact between the first reagent and the second reagent or after the contact between the solid composition and the liquid. In other embodiments, the pH of the formed liquid can become about lower than 1, 2, 3, 4, 5, 6, 7, or 8 within about 1 minute after the contact between the first reagent and the second reagent or after the contact between the solid composition and the liquid. The liquid that comprises peroxyformic acid can maintain the pH ranging from about 0 to about 8 for any suitable time after the contact between the first reagent and the second reagent, or after the contact between the composition and a liquid. In some embodiments, the liquid that comprises peroxy formic acid maintains the pH ranging from about 0 to about 8 from about 1 second to about 10 hours after the contact between the first reagent and the second reagent or after the contact between the composition and a liquid. For example, the liquid that comprises peroxy formic acid can maintain the pH at about 0, 1, 2, 3, 4, 5, 6, 7, or 8 from about 1 second to about 10 hours after the contact between the first reagent and the second reagent or after the contact between the composition and a liquid. In another example, the liquid that comprises peroxyformic acid can maintain the pH ranging from about 0 to about 8 for about 1 second, 2 seconds, 3 seconds, 4 seconds, 5 seconds, 6 seconds, 7 seconds, 8 seconds, 9 seconds, 10 seconds, 20 seconds, 30 seconds, 40 seconds, 50 seconds. 1 minute, 2 minutes, 3 minutes, 4 minutes, 5 minutes, 6 minutes, 7 minutes, 8 minutes, 9 minutes, 10 minutes, 20 minutes, 30 minutes, 40 minutes, 50 minutes, 1 hour, 2 hours, 3 hours, 4 hours, 5 hours, 6 hours, 7 hours, 8 hours, 9 hours, or 10 hours.

Additional description of preferred embodiments of peroxyformic acid forming compositions, methods of forming the same, and methods of using the same are disclosed in U.S. Publication No./Ser. No. 14/973,389 titled "Generation of Peroxyformic Acid through Polyhydric Alcohol Formate", which is herein incorporated by reference in its entirety.

Additional Functional Ingredients

The components of the peroxycarboxylic acid compositions employing the self-indicating chemistry compositions can further include various functional components suitable for use in forming the peroxycarboxylic acid compositions and/or the sanitizing, cleaning and disinfecting applications of use thereof. In some embodiments, the peroxycarboxylic acid compositions employing the self-indicating chemistry compositions including the self-indicating chemistry compositions and the first and second reagents for the peroxycarboxylic acid forming compositions make up a large amount, or even substantially all of the total weight of the peroxycarboxylic acid compositions. For example, in some embodiments few or no additional functional ingredients are disposed therein.

In other embodiments, additional functional ingredients may be included in the compositions. The functional ingredients provide desired properties and functionalities to the compositions. For the purpose of this application, the term "functional ingredient" includes a material that when dispersed or dissolved in a use and/or concentrate solution, such as an aqueous solution, provides a beneficial property in a particular use. Some particular examples of functional materials are discussed in more detail below, although the particular materials discussed are given by way of example only, and that a broad variety of other functional ingredients may be used.

In other embodiments, the compositions may further include a catalyst (e.g. enzyme), stabilizing agents, pH buffering agents, acidulant, defoaming agents, anti-redeposition agents, bleaching agents, solubility modifiers, dispersants, wetting agents, metal protecting agents, corrosion inhibitors, additional sequestrants and/or chelating agents, fragrances and/or dyes, rheology modifiers or thickeners, hydrotropes or couplers, buffers, solvents and the like.

In an aspect, the peroxycarboxylic acid forming compositions can further comprise a wetting agent. Wetting agents function to increase the surface contact or penetration activity of the antimicrobial composition of the invention. Wetting agents which can be used in the composition of the invention include any of those constituents known within the art to raise the surface activity of the composition of the invention. In an exemplary aspect, the wetting agent is a sulfonic acid or salt thereof (e.g., dodecylbenzene sulfonic acid, sodium salt). In certain embodiments, the wetting agent is present in amounts from about 0.001 to about 10 wt-% wetting agent, about 0.01 to about 1 wt-% wetting agent, about 0.01 to about 0.5 wt-% wetting agent, or about 0.1 to about 0.5 wt-% wetting agent.

In an aspect, the peroxycarboxylic acid forming compositions can further comprise an acidulant. In an aspect, the acidulant is included in the second reagent with hydrogen peroxide. Any suitable acid can be included in the compositions as an acidulant. In an embodiment the acidulant is an acid or an aqueous acidic solution. In an embodiment, the acidulant includes an inorganic acid. In some embodiments, the acidulant is a strong mineral acid. Suitable inorganic acids include, but are not limited to, sulfuric acid, sodium bisulfate, phosphoric acid, nitric acid, hydrochloric acid. In some embodiments, the acidulant includes an organic acid. Suitable organic acids include, but are not limited to, methane sulfonic acid, ethane sulfonic acid, propane sulfonic acid, butane sulfonic acid, xylene sulfonic acid, cumene sulfonic acid, benzene sulfonic acid, formic acid, acetic acid, mono, di, or tri-halocarboyxlic acids, picolinic acid, dipicolinic acid, and mixtures thereof. In certain embodiments, the acidulant is present in amounts from about 0.001 to about 50 wt-% acidulant, about 0.001 to about 10 wt-%, about 0.01 to about 1 wt-% acidulant, or about 0.05 to about 0.5 wt-%.

In an aspect, the peroxycarboxylic acid forming compositions can further comprise a catalyst or an enzyme that catalyzes formation of the peroxycarboxylic acid from the ester of a polyhydric alcohol and carboxylic acid, and hydrogen peroxide. Any suitable catalyst or enzyme can be included in the peroxycarboxylic acid forming composition, e.g., a perhydrolytic enzyme, lipase, coronase, termanyl or esperease. The catalyst or an enzyme can be comprised in any suitable part of the peroxycarboxylic acid forming compositions. In some embodiments, the first reagent comprises the catalyst or enzyme. In other embodiments, the second reagent comprises the catalyst or enzyme. In still other embodiments, the peroxycarboxylic acid forming compositions can further comprise a third reagent that comprises the catalyst or enzyme. In yet other embodiments, the solid composition comprises the catalyst or enzyme.

In an aspect, the peroxycarboxylic acid forming compositions can further comprise a stabilizing agent for the peroxycarboxylic acid, a stabilizing agent for hydrogen In an aspect, the peroxycarboxylic acid forming compositions can further comprise peroxide, and/or a pH buffering agent. The present peroxycarboxylic acid forming compositions can comprise any suitable pH buffering agent stabilizing agent. Exemplary stabilizing agents include a phosphonate salt(s) and/or a heterocyclic dicarboxylic acid, e.g., dipicolinic acid. In some embodiments, the stabilizing agent is pyridine carboxylic acid based stabilizers, such as picolinic acid and salts, pyridine-2,6-dicarboxylic acid and salts, and phosphonate based stabilizers, such as phosphoric acid and salts, pyrophosphoric acid and salts and most commonly 1-hydroxyethylidene-1,1-diphosphonic acid (HEDP) and salts. In other embodiments, the present peroxycarboxylic acid forming compositions comprise two or more stabilizing agents, e.g., HEDP and 2,6-pyridinedicarboxylic acid (DPA). In an aspect the stabilizing agent(s) can be comprised in any suitable part of the present peroxycarboxylic acid forming compositions. In some embodiments, the first reagent comprises a stabilizing agent for the peroxycarboxylic acid and/or a pH buffering agent. In other embodiments, the second reagent comprises a stabilizing agent for hydrogen peroxide. In still other embodiments, the present peroxycarboxylic acid forming compositions can further comprise a third reagent that comprises a stabilizing agent for the peroxycarboxylic acid, a stabilizing agent for hydrogen peroxide, and/or a pH buffering agent. In yet other embodiments, the solid composition comprises a stabilizing agent for peroxyformic acid, a stabilizing agent for hydrogen peroxide, and/or a pH buffering agent.

In an aspect, the peroxycarboxylic acid forming compositions can further comprise any suitable pH buffering agent. The pH buffer reagent can include any reagent that is compatible with the ester(s) in the peroxycarboxylic acid forming compositions. Exemplary buffer agents suitable for using with a liquid ester can be an organic amine, such as triethanol amine, imidazole, etc. Exemplary buffer agents suitable for using with a solid form of ester include a broader range of buffers, such as a carbonate salt, a phosphate salt, etc. The pH buffer reagent can be comprised in any suitable part of the present peroxyformic acid forming compositions. In some embodiments, the first reagent comprises a pH buffering agent. In other embodiments, the peroxycarboxylic acid forming compositions can further comprise a third reagent that comprises a pH buffering agent. In still other embodiments, the solid composition comprises a pH buffering agent.

In an aspect, the peroxycarboxylic acid forming compositions can further comprise any suitable stabilizing agent for hydrogen peroxide. Exemplary stabilizing agents for hydrogen peroxide include phosphonates, heterocyclic carboxylic acids and the mixtures thereof. In some embodiments, stabilizing agents for hydrogen peroxide can be Dequest 2010, Dequest 2066, Dipicolinic acids, etc. The stabilizing agent for hydrogen peroxide can be comprised in any suitable part of the peroxycarboxylic acid forming compositions. In some embodiments, the second reagent comprises a stabilizing agent for hydrogen peroxide. In other embodiments, the peroxycarboxylic acid forming compositions can further comprise a third reagent that comprises a stabilizing agent for hydrogen peroxide. In still other embodiments, the solid composition comprises a stabilizing agent for hydrogen peroxide.

In preferred embodiments, the compositions do not include perhydrolysis enzymes, such as members of family 7 of the carbohydrate esterases (CE-7) or a perhydrolysis enzyme, such as those disclosed for example in U.S. Patent Publication 2013/0289113, which is herein incorporated by reference in its entirety.

In preferred embodiments, the compositions do not include iodide, iodine or other components destructive to the peroxycarboxylic acid generated in situ.

In further embodiments, the latent peracid selective dyes do not include substrates for detecting peroxidase in ELISA (Enzyme Linked Immmuno Assay) applications. Without being limited to a particular mechanism of theory, the peroxidase does not behave as a perhydrolyase and instead generates OH radicals simulating peracids.

Alkalinity Source

The peroxycarboxylic acid forming compositions may require pH adjustment with an alkalinity source. In an exemplary aspect, in the event a reagent of the self-indicating peracid chemistry includes an acidic component, such as a wetting agent, an alkalinity source may be desirable to increase the strongly acidic pH to ensure the perhydrolysis reaction to generate the peroxycarboxylic acid is not slowed.

Suitable sources of alkalinity can include, but is not limited to, an alkaline metal hydroxide, an alkaline earth metal hydroxide, an alkali metal silicate, an alkali metal carbonate, borates, amines, amides or other basic nitrogen sources and mixtures thereof. Suitable alkaline metal hydroxides include, but are not limited to, sodium hydroxide, potassium hydroxide and mixtures thereof. Suitable alkaline earth metal hydroxides include, but are not limited to, magnesium hydroxide, calcium hydroxide and mixtures and derivatives thereof. Suitable alkali metal silicates include but are not limited to, sodium silicate and derivatives thereof. Suitable amines include, but are not limited to, primary, secondary or tertiary amines and diamines carrying at least one nitrogen linked hydrocarbon group, which represents a saturated or unsaturated linear or branched alkyl group having at least 1 carbon atom. Amines may further include alkanolamines including, for example, monoethanolamine, monoisopropanolamine, diethanolamine, diisopropanolamine, triethanolamine, triisopropanolamine and the like.

The source of alkalinity can be added to the self-indicating chemistry compositions to provide the desired pH of the use-solution. In some embodiments, the alkalinity source is added to achieve a pH of from about 5 to about 10.

Kits

The self-indicating chemistry composition may be provided in a kit or multi-part system. In an aspect, a two part spray bottle provides a first portion of a self-indicating chemistry composition and a second portion containing a peroxycarboxylic acid or a peroxycarboxylic acid generating composition.

In an aspect, a two-part spray bottle is provided for point of use application for hard surface disinfection or sanitizing for consumer and/or industrial applications.

In an aspect, a two-part spray bottle is suitable to provide compositions in a variety of delivery forms, including for example, liquids, mist, etc. for consumer and/or industrial applications.

Other Delivery Systems

The self-indicating chemistry composition may be provided in various forms wherein multi-part systems are provided, preferably two-part system.

In an aspect, a two part system may be provided in the form of separate spray bottles, separate storage containers and a device for combining the containers, a pre-soaked wipe (or other linen) to be combined with a second liquid chemistry, or the like.

Kits

In an aspect, the self-indicating chemistry can be provided in a kit for a customer or particular application of use. A kit is particularly useful when provided with a color indication system which correlates the observed color indicator with a range of concentration of the peroxycarboxylic acid composition. A kit can include instructions for use. In a further aspect, a kit can include information for the correlation of a desired wavelength of a visual indicator to a particular color on a color wheel which is correlated to a ppm concentration of the peroxycarboxylic acid concentration. The colors on a color wheel can be standardized to a reflective color or to a pantone color number (equivalent to a concentration of ppm).

Methods of Indication

Methods of indicating concentrations of a peroxycarboxylic acid compositions are provided by the self-indicating chemistry compositions of the invention. In an aspect, the methods including providing a self-indicating chemistry composition to a peroxycarboxylic acid composition generated by perhydrolysis in situ, and obtaining various visual indicators of the concentration of peroxycarboxylic acid composition at points of time. In an aspect, the self-indicating chemistry compositions provide visual indicators to a user when there is at least an initial efficacious level of the peroxycarboxylic acid (i.e. ready to use), and a subsequent visual indicator when the concentration of the peroxycarboxylic acid is no longer at an efficacious level (i.e. unsuitable for use). In an aspect, the visual indicators include red, yellow, blue and/or green colors having a correlation to a predetermined concentration of a peroxycarboxylic acid. In an aspect, the visual indicators include red, yellow, and green colors having a correlation to a predetermined concentration of a peroxycarboxylic acid. In another aspect, the visual indicators include yellow, blue and green colors having a correlation to a predetermined concentration of a peroxycarboxylic acid. The methods of the invention can be further achieved through the use of a kit for providing the indication of concentrations of a peroxycarboxylic acid composition.

The method of indicating concentrations of a peroxycarboxylic acid compositions includes the combination of self-indicating chemistry composition to provide a combination of dyes. The self-indicating chemistry composition is provided in a two-part system, including a first part comprising a combination of dyes and an ester precursor for peroxycarboxylic acid generation, and a second part comprising hydrogen peroxide. Additional components of the two-part system are disclosed in the compositions according to the invention. Without being limited to a particular mechanism of action, the separation of the two-part system prevents the hydrogen peroxide from prematurely reacting with the ester precursor.

In an aspect, the combination of dyes have an initial blue color indicating the presence of the self-indicating chemistry composition with a peroxycarboxylic acid composition or a peroxycarboxylic acid generating composition. In an aspect, the visual indicator of the blue dye indicates the presence of the self-indicating chemistry composition within the peroxycarboxylic acid composition or peroxycarboxylic acid generating composition. Without being limited to a particular mechanism of action, the blue visual indicator does not directly correlate to any concentration of the peroxycarboxylic acid, instead, the blue visual indicator provide by the background dye serves as a background color and a mixing indicator.

In an optional aspect, a red color can be used as an initial indicator. The red color is bleached out of the system promptly upon the initiation of the perhydrolysis reaction and is therefore an optional component of the system.

The method of indicating concentrations of a peroxycarboxylic acid compositions includes at least a second visual indicator. In an aspect, the combination of self-indicating chemistry compositions provides a change from a blue color to a green color to indicate a peroxycarboxylic acid composition is "ready" for use. In an aspect, the change from blue to green indicates a concentration of at least about 1 ppm to 1,000 ppm of the peroxycarboxylic acid.

In an aspect, the peroxycarboxylic acid composition concentrations measured using the self-indicating chemistry compositions provide a user with a visual indicator to confirm whether a desired peroxycarboxylic acid concentration is retained in a composition. In some embodiments, a visual indicator is provided to confirm a peroxycarboxylic acid composition has achieved a suitable concentration, as may be referred to as a minimal inhibitory concentration (MIC) of a particular antimicrobial agent for a surface of contaminated system. In some aspects, a level from about 1 ppm to about 1,000 ppm, e.g., 1-10 ppm, 10-20 ppm, 20-30 ppm, 30-40 ppm, 40-50 ppm, 50-60 ppm, 60-70 ppm, 70-80 ppm, 80-90 ppm, 90-100 ppm, 100-150 ppm, 150-200 ppm, 200-250 ppm, 250-300 ppm, at least about 270 ppm, or at least about 300 ppm, 300-350 ppm, 350-400 ppm, 400-450 ppm, 450-500 ppm, 500-550 ppm, 550-600 ppm, 600-650 ppm, 650-700 ppm, 700-750 ppm, 750-800 ppm, 800-850 ppm, 850-900 ppm, 900-950 ppm, or 950-1,000 ppm.

In an aspect, the peroxycarboxylic acid composition concentrations measured using the self-indicating chemistry compositions provide a user with a visual indicator to confirm whether a desired peroxycarboxylic acid concentration is obtained in a composition over a pre-determined amount of time. In some embodiments, a visual indicator is provided to confirm a peroxycarboxylic acid composition has achieved a suitable concentration, such as an MIC, within about 30 seconds to about 30 minutes, within about 30 seconds to about 10 minutes, from about 30 seconds to about 90 seconds, or from about 10 minutes to about 20 minutes. In some aspects, a level from about 1 ppm to about 1,000 ppm is detected with the time frames, e.g., 1-10 ppm, 10-20 ppm, 20-30 ppm, 30-40 ppm, 40-50 ppm, 50-60 ppm, 60-70 ppm, 70-80 ppm, 80-90 ppm, 90-100 ppm, 100-150 ppm, 150-200 ppm, 200-250 ppm, 250-300 ppm, at least about 270 ppm, or at least about 300 ppm, 300-350 ppm, 350-400 ppm, 400-450 ppm, 450-500 ppm, 500-550 ppm, 550-600 ppm, 600-650 ppm, 650-700 ppm, 700-750 ppm, 750-800 ppm, 800-850 ppm, 850-900 ppm, 900-950 ppm, or 950-1,000 ppm.

In an exemplary aspect, the peroxycarboxylic acid composition concentrations measured using the self-indicating chemistry compositions provide a user with a visual indicator to confirm a desired peroxycarboxylic acid concentration of from about 1 to 100 ppm is obtained in a composition between about 30 seconds to about 90 seconds. In a further exemplary aspect, the peroxycarboxylic acid composition concentrations measured using the self-indicating chemistry compositions provide a user with a visual indicator to confirm a desired peroxycarboxylic acid concentration of from about 1 to 10 ppm is obtained in a composition between about 10 minutes to about 20 minutes.

The method of indicating concentrations of a peroxycarboxylic acid composition includes at least a third visual indicator. In an aspect, the combination of self-indicating chemistry compositions provides a change from a green color to a yellow color to indicate a peroxycarboxylic acid composition or concentration is no longer suitable for use or an "exhausted" composition.

In an aspect, the peroxycarboxylic acid composition concentrations measured using the self-indicating chemistry compositions provide a user with a visual indicator to confirm when a desired peroxycarboxylic acid concentration is no longer retained. In some embodiments, a visual indicator is provided to confirm when a peroxycarboxylic acid composition has reduced by a percentage over a period of time. In some aspects, a visual indicator is provided to indicate a desired peroxycarboxylic acid concentration has reduced by 10%, 15%, 20%, 25%, 30%, 35%, 40%, 45%, 50%, or greater from the initial peroxycarboxylic acid activity or concentration on a predetermined amount of time, which correlates with a visual indicator based on the fading or changing in color of a selected dye of the self-indicating peroxycarboxylic acid chemistry.

In an aspect, the visual indicators provided according to the invention may be further combined with a system to monitor the peroxycarboxylic acid compositions. The compositions can be further monitored in any suitable manner. For example, sensor technologies may be used in combination with an optical sensor technology. In an aspect, and without limiting the scope of the monitoring which one skilled in the art will ascertain based upon the disclosure herein, the monitor, such as a sensor, may also be used to determine the concentrations of peroxycarboxylic acid or other components of the composition (e.g. hydrogen peroxide, or other additional ingredients, such as acidulants, one or more stabilizing agents, surfactants, adjuvants, solvents, additional antimicrobial agents or other ingredients which may be present in the composition).

In an alternative aspect, the methods of indicating concentrations of a peroxycarboxylic acid composition could be employed for detected maintained peroxycarboxylic acid concentration in a ready-to-use or pre-formed composition. In such an embodiment, the visual indicators may include for example, a two or more color system to indicate a ready-to-use, or first, desired concentration of the peroxycarboxylic acid, and thereafter a second visual indicator once the peroxycarboxylic acid concentration drops below a threshold concentration suitable for a particular use.

Methods of Use

In an aspect, the self-indicating chemistry compositions and peroxycarboxylic acid compositions employing the self-indicating chemistry compositions are suitable for use in industries and applications where sanitizing, cleaning or disinfecting compositions are employed. Beneficially, the self-indicating chemistry compositions are non-destructive assays for peroxycarboxylic acid compositions. As a result, the self-indicating chemistry compositions unexpectedly provide a non-destructive mechanism to monitor biocide concentrations without destruction of the biocide itself, serving as a benign probe or assay of the chemistries. As referred to herein, non-destructive means that the dyes do not result in any more than stoichiometric damage or loss of the peroxycarboxylic acid concentration. In an aspect, non-destructive further means that the dyes do not result in loss of the peroxycarboxylic acid concentration at a rate that exceeds the ongoing generation of peroxycarboxylic acid in an in situ reaction for the ongoing generation of the biocide.

In further aspects, the self-indicating chemistry compositions unexpectedly provide a stabilizing effect on the in situ generated peroxycarboxylic acid compositions. In an aspect the peroxycarboxylic acid compositions employing the self-indicating chemistry compositions according to the invention result in at least about 1%, 2%, 3%, 4%, 5%, 6%, 7%, 8%, 9%, or at least a 10% improvement in peroxycarboxylic acid stabilization in comparison to an in situ generated peroxycarboxylic acid composition not employing the self-indicating chemistry. In other aspects, the peroxycarboxylic acid compositions employing the self-indicating chemistry compositions according to the invention result in at least about 10%, or at least about 15%, or at least about 20%, or at least about 25% improvement in peroxycarboxylic acid stabilization in comparison to an in situ generated peroxycarboxylic acid composition not employing the self-indicating chemistry. As referred to herein, the improvement in peroxycarboxylic acid stabilization refers to the concentration of peroxycarboxylic acid (ppm) retained in the composition over time, such as over 5 minutes, 10 minutes, 15 minutes, 20 minutes or longer from the in situ reaction to generate the peroxycarboxylic acid composition.

In an aspect, use of a peroxycarboxylic acid for sanitizing, cleaning or disinfecting, including use on a target surface, such as hard surfaces is particularly suitable for employing the methods of indication disclosed herein. Applications to a target, including a hard surface, include contacting a target with an effective amount of peroxycarboxylic acid, wherein the effective amount is indicated to a user by the self-indicating chemistry composition, and said contacting step lasts for sufficient time to stabilize or reduce microbial population in and/or on said target or said treated target composition. Examples include at least a portion of a medium, a container, a surface, an equipment, including those in a facility for producing, growing, holding, processing, packaging, storing, or transporting a food or beverage item or pulp, transporting, preparing, cooking or serving a food or beverage item or the plant item. Further examples, include any medium, a surface, a container, an equipment, or a system in a health care facility, e.g., a physical office or a hospital. A still further example includes a biofilm on a surface.

In further aspects, the target or surface may include any suitable food item. For example, the food item can be an animal product, e.g., an animal carcass or an egg, a fruit item, a vegetable item, or a grain item. In still further aspects, the target or surface may include any suitable plant item. In some embodiments, the plant item is a grain, fruit, vegetable or flower plant item. In other embodiments, the plant item is a living plant item or a harvested plant item. In still other embodiments, the plant item comprises a seed, a tuber, a growing plant, a cutting, or a root stock. In yet other embodiments, the present methods are used for treating a living plant tissue comprising treating the plant tissue with the above composition in a diluted level to stabilize or reduce microbial population in and/or on the plant tissue.

In some aspects, the present methods are particularly suitable for treating a target that is at least a portion of a container, an equipment, a system or a facility for holding, processing, packaging, storing, transporting, preparing, cooking or serving the food item or the plant item. In some embodiments, the target is at least a portion of a container, an equipment, a system or a facility for holding, processing, packaging, storing, transporting, preparing, cooking or serving a meat item, a fruit item, a vegetable item, or a grain item. In other embodiments, the target is at least a portion of a container, an equipment, a system or a facility for holding, processing, packaging, storing, or transporting an animal carcass. In still other embodiments, the target is at least a portion of a container, an equipment, a system or a facility used in food processing, food service or health care industry. In yet other embodiments, the target is at least a portion of a fixed in-place process facility. An exemplary fixed in-place process facility can comprise a milk line dairy, a continuous brewing system, a pumpable food system or a beverage processing line. In yet other embodiments, the solid surface is an inanimate solid surface which may be contaminated by a biological fluid, e.g., a biological fluid comprising blood, other hazardous body fluid, or a mixture thereof. In other embodiments, the solid surface can be a contaminated surface. An exemplary contaminated surface can comprise the surface of food service wares or equipment, or the surface of a fabric.

The present methods may be useful in the cleaning or sanitizing of containers, processing facilities, or equipment in the food service or food processing industries. The present methods may be used on food packaging materials and equipment, including for cold or hot aseptic packaging. Examples of process facilities in which the present methods may be employed include a milk line dairy, a continuous brewing system, food processing lines such as pumpable food systems and beverage lines, etc. Food service wares may be disinfected with the present methods. For example, the present methods may also be used on or in ware wash machines, dishware, bottle washers, bottle chillers, warmers, third sink washers, cutting areas (e.g., water knives, slicers, cutters and saws) and egg washers. Particular treatable surfaces include packaging such as cartons, bottles, films and resins; dish ware such as glasses, plates, utensils, pots and pans; ware wash machines; exposed food preparation area surfaces such as sinks, counters, tables, floors and walls; processing equipment such as tanks, vats, lines, pumps and hoses (e.g., dairy processing equipment for processing milk, cheese, ice cream and other dairy products); and transportation vehicles. Containers include glass bottles, PVC or polyolefin film sacks, cans, polyester, PEN or PET bottles of various volumes (100 ml to 2 liter, etc.), one gallon milk containers, paper board juice or milk containers, etc.

In an aspect, the peroxycarboxylic acid contacts a target for sanitizing, cleaning or disinfecting at any suitable level of said peroxycarboxylic acid, e.g., about 0.1-1 ppm, 1-10 ppm, 10-20 ppm, 20-30 ppm, 30-40 ppm, 40-50 ppm, 50-60 ppm, 60-70 ppm, 70-80 ppm, 80-90 ppm, 90-100 ppm, 100-150 ppm, 150-200 ppm, 200-250 ppm, 250-300 ppm, 300-350 ppm, 350-400 ppm, 400-450 ppm, 450-500 ppm, 500-550 ppm, 550-600 ppm, 600-650 ppm, 650-700 ppm, 700-750 ppm, 750-800 ppm, 800-850 ppm, 850-900 ppm, 900-950 ppm, 950-1,000 ppm, 1,000-1,500 ppm, 1,500-2,000 ppm, 2,000-2,500 ppm, 2,500-3,000 ppm, 3,000-3,500 ppm, 3,500-4,000 ppm, 4,000-4,500 ppm, or 4,500-5,000 ppm, 5,000-5,500 ppm, 5,500-6,000 ppm, 6,000-6,500 ppm, 6,500-7,000 ppm, 7,000-7,500 ppm, 7,500-8,000 ppm, 8,000-8,500 ppm, 8,500-9,000 ppm, 9,000-9,500 ppm, or 9,500-10,000 ppm of peroxycarboxylic acid.

In an aspect, the peroxycarboxylic acid composition is used for such target or hard surface treatment until the self-indicating chemistry compositions provides a user with a visual indicator that the suitable level (concentration) or percentage of the peroxycarboxylic acid is retained in the composition. In some embodiments, the peroxycarboxylic acid composition retains at least about 50%, 55%, 60%, 65%, 70%, 75%, 80%, 85% or 90% of the initial peroxycarboxylic acid activity before a user receives the visual indication that the peroxycarboxylic acid composition is no longer suitable for use.

The present methods may be useful in treating a water source as a target. The present methods can be used to treat water, and the present methods can comprise providing an effective amount of peroxycarboxylic acid formed using the above methods to a water source in need of treatment to form a treated water source, wherein said treated water source comprises from about 0.1-1 ppm, 1-10 ppm, 10-20 ppm, 20-30 ppm, 30-40 ppm, 40-50 ppm, 50-60 ppm, 60-70 ppm, 70-80 ppm, 80-90 ppm, 90-100 ppm, 100-150 ppm, 150-200 ppm, 200-250 ppm, 250-300 ppm, 300-350 ppm, 350-400 ppm, 400-450 ppm, 450-500 ppm, 500-550 ppm, 550-600 ppm, 600-650 ppm, 650-700 ppm, 700-750 ppm, 750-800 ppm, 800-850 ppm, 850-900 ppm, 900-950 ppm, or 950-1,000 ppm. The present methods can be used to treat any suitable water source. For example, a water source in need of treatment can be fresh water, pond water, sea water, produced water, paper manufacturing water, tower water or a combination thereof. In some embodiments, the tower water is cooling water and the treated water source comprises from about 1 ppm to about 10 ppm of the peroxyformic acid, e.g., about 1-2 ppm, 2-3 ppm, 3-4 ppm 4-5 ppm, 5-6 ppm, 6-7 ppm, 7-8 ppm, 8-9 ppm, or 9-10 ppm peroxyformic acid. The contacting step can last any suitable amount of time, e.g., about 1-2 minutes, 2-3 minutes, 3-4 minutes, 4-5 minutes, 5-6 minutes, 6-7 minutes, 7-8 minutes, 8-9 minutes, or 9-10 minutes. The contacting step can be conducted at suitable temperature range. For example, the contacting step can be conducted at a temperature ranging from about 0° C. to about 60° C., e.g., about 0° C.-1° C., 1° C.-2° C., 2° C.-3° C., 3° C.-4° C., 4° C.-5° C., 5° C.- 10° C., 10° C.-15° C., 15° C.-20° C., 20° C.-25° C., 25° C.-30° C., 30° C.-35° C., 35° C.-40° C., 40° C.-45° C., 45° C.-50° C., 50° C.-55° C., or 55° C.-60° C.

In some embodiments, the present methods can be used to treat a water source used in oil or gas drilling operation. For example, the present methods can be used to treat a water source used in an operation of induced hydraulic fracturing (hydrofracturing or fracking). The water source can comprise a friction reducer or a viscosity enhancer. The present methods can be used to treat a water source to form a treated water source that comprises from about 1 ppm to about 10 ppm of the peroxyformic acid, e.g., about 1-2 ppm, 2-3 ppm, 3-4 ppm, 4-5 ppm, 5-6 ppm, 6-7 ppm, 7-8 ppm, 8-9 ppm, or 9-10 ppm or greater peroxycarboxylic. The present methods can further comprise disposing of the treated water source. The present methods can further comprise directing the treated water source into a subterranean environment, e.g., a subterranean environment that comprises a well in a gas and/or oil.

The methods include any suitable manner of applying the peroxycarboxylic acid compositions. In some embodiments, the peroxycarboxylic acid can be applied to a target by means of a spray, a fog, or a foam, or by dipping all or part of the target in a composition comprising the peroxycarboxylic acid. In some embodiments, the peroxycarboxylic acid composition is applied to the target by means of a spray, a fog, or a foam. In other embodiments, the diluted peroxycarboxylic acid is applied to the target by applying in the form of a thickened or gelled solution. In still other embodiments, all or part of the target is dipped in the peroxycarboxylic acid composition. The target and/or the peroxycarboxylic acid composition can be subject to any suitable movement to help or facilitate the contact between the target and the peroxycarboxylic acid composition. In some embodiments, the peroxycarboxylic acid composition can be agitated. In other embodiments, the peroxycarboxylic acid composition can be sprayed onto a target.

The contacting step of the present methods can last for any suitable amount of time. In some embodiments, the contacting step can last for at least about 10 seconds. For example, the contacting step can last for at least about 10, 20, 30, 40, 50 seconds, 1 minute, 1-2 minutes, 2-3 minutes, 3-4 minutes, 4-5 minutes, 5-6 minutes, 6-7 minutes, 7-8 minutes, 8-9 minutes, or 9-10 minutes, 10-15 minutes, 15-20 minutes, 20-25 minutes, 25-30 minutes, 30-40 minutes, 40-50 minutes, 50-65 minutes, 1-2 hours, 2-3 hours, 3-4 hours, 4-5 hours, 5-6 hours, 6-7 hours, 7-8 hours, 8-9 hours, or 9-10 hours, 16 hours, 1 day. 3 days, 1 week, or longer.

The present methods can be used to reduce microbial population in and/or on the target or the treated target composition by any suitable magnitude. In some embodiments, the present methods can be used to reduce microbial population in and/or on the target or surface by at least one log 10, two log 10, three log 10, four log 10, five log 10, or more. In other embodiments, the level of a microorganism, if present in and/or on the target or surface, can be stabilized or reduced by the present methods. For example, at least 10%, 20%, 30%, 40%, 50%, 60%, 70%, 80%, or 90% or more of the microorganism can be killed, destroyed, removed and/or inactivated by the present methods. The present methods can be used to reduce population of any suitable microbe(s) by any suitable magnitude. The peroxycarboxylic acid compositions provide broad spectrum bactericidal and fungistatic activity. For example, the peroxycarboxylic acid compositions provide broad spectrum activity against wide range of different types of microorganisms (including both aerobic and anaerobic microorganisms), including bacteria, yeasts, molds, fungi, algae, and other problematic microorganisms. Exemplary microorganisms susceptible to the peroxycarboxylic acid compositions include, gram positive bacteria (e.g., *Staphylococcus aureus, Bacillus* species (sp.) like *Bacillus subtilis, Clostridia* sp.), gram negative bacteria (e.g., *Escherichia coli, Pseudomonas* sp., *Klebsiella pneumoniae, Legionella pneumophila, Enterobacter* sp., *Serratia* sp., *Desulfovibrio* sp., and *Desulfotomaculum* sp.), yeasts (e.g., *Saccharomyces cerevisiae* and *Candida albicans*), molds (e.g., *Aspergillus niger,*

*Cephalosporium acremonium, Penicillium notatum*, and *Aureobasidium pullulans*), filamentous fungi (e.g., *Aspergillus niger* and *Cladosporium resinae*), algae (e.g., *Chlorella vulgaris, Euglena gracilis*, and *Selenastrum capricornutum*), and other analogous microorganisms and unicellular organisms (e.g., phytoplankton and protozoa).

In an aspect, the present methods provide an indication of peroxycarboxylic acid concentration suitable for the biocidal efficacy against *C. difficiles* spores, namely at least about 270 ppm, or preferably at least about 300 ppm peroxycarboxylic acid.

The present methods can be conducted at any suitable temperature range. In some embodiments, the present methods can be conducted at a temperature ranging from about 0° C. to about 70° C., e.g., from about 0° C. to about 4° C. or 5° C., from about 5° C. to about 10° C., from about 11° C. to about 20° C., from about 21° C. to about 30° C., from about 31° C. to about 40° C., including at about 37° C., from about 41° C. to about 50° C., from about 51° C. to about 60° C., or from about 61° C. to about 70° C. In other embodiments, the present methods can be conducted at a temperature at or lower than 0° C.

In an exemplary method of use, the compositions are useful in the cleaning or sanitizing of processing facilities or equipment in the food service, food processing or health care industries. Examples of process facilities in which the present methods can be employed include a milk line dairy, a continuous brewing system, food processing lines such as pumpable food systems and beverage lines, etc. Food service wares can also be disinfected with the present methods. The present methods are also useful in sanitizing or disinfecting solid surfaces such as floors, counters, furniture, medical tools and equipment, etc., found in the health care industry. Such surfaces often become contaminated with liquid body spills such as blood, other hazardous body fluids or mixtures thereof. Generally, the actual cleaning of the in-place system or other surface (i.e., removal of unwanted offal therein) can be accomplished with a different material such as a formulated detergent which is introduced with heated water. After this cleaning step, the peroxycarboxylic acid composition can be applied or introduced into the system at a use solution concentration in unheated, ambient temperature water. In some embodiments, the peroxycarboxylic acid composition is found to remain in solution in cold (e.g., 40° F./4° C.) water and heated (e.g., 140° F./60° C.) water. Although it is not normally necessary to heat the aqueous use solution of the peroxycarboxylic acid composition, under some circumstances heating may be desirable to further enhance its antimicrobial activity.

In another exemplary method of use, a method of sanitizing substantially fixed in-place process facilities comprises the following steps. The peroxycarboxylic acid composition of the present invention is introduced into the process facilities at a temperature in the range of about 4° C. to about 60° C. After introduction of the use solution, the solution is circulated throughout the system for a time sufficient to sanitize the process facilities (i.e., to kill undesirable microorganisms). After the system has been sanitized by means of the present composition, the use composition or solution is drained from the system. Upon completion of the sanitizing step, the system optionally may be rinsed with other materials such as potable water. The present composition is preferably circulated through the process facilities for 10 minutes or less.

In yet another exemplary method of use, the peroxycarboxylic acid compositions may also be employed by dipping food processing equipment into the diluted (or use) composition or solution of the present invention, soaking the equipment for a time sufficient to sanitize the equipment, and wiping or draining excess solution off the equipment. The composition may be further employed by spraying or wiping food processing surfaces with the use solution, keeping the surfaces wet for a time sufficient to sanitize the surfaces, and removing the excess composition or solution by wiping, draining vertically, vacuuming, etc.

In still other exemplary methods of use, the present peroxycarboxylic acid composition may also be used in a method of sanitizing hard surfaces such as institutional type equipment, utensils, dishes, health care equipment or tools, and other hard surfaces. The present peroxyformic acid composition may also be employed in sanitizing clothing items or fabric which has become contaminated. The peroxycarboxylic acid composition is contacted with any of the above contaminated surfaces or items at use temperatures in the range of about 4° C. to about 60° C. for a period of time effective to sanitize, disinfect, or sterilize the surface or item.

All publications and patent applications in this specification are indicative of the level of ordinary skill in the art to which this invention pertains. All publications and patent applications are herein incorporated by reference to the same extent as if each individual publication or patent application was specifically and individually indicated as incorporated by reference.

EXAMPLES

Embodiments of the present invention are further defined in the following non-limiting Examples. It should be understood that these Examples, while indicating certain embodiments of the invention, are given by way of illustration only. From the above discussion and these Examples, one skilled in the art can ascertain the essential characteristics of this invention, and without departing from the spirit and scope thereof, can make various changes and modifications of the embodiments of the invention to adapt it to various usages and conditions. Thus, various modifications of the embodiments of the invention, in addition to those shown and described herein, will be apparent to those skilled in the art from the foregoing description. Such modifications are also intended to fall within the scope of the appended claims.

Example 1

The two-part chemistry system of was evaluated for its ability to provide self-indicating detection of changes in concentration of peroxycarboxylic acid concentrations in a solution produced in situ. In this example performic acid was generated in situ as the peroxycarboxylic acid composition.

Part (I):

| | |
|---|---|
| Glyceryl formate | 97.0996% |
| Imidazole | 2.7673% |
| 3,3',5,5'-Tetramethylbenzidine (TMB) | 0.0466% |
| 2,2'-azino-bis(3-ethylbenzothiazoline-6-sulphonic acid) (ABTS) | 0.0748% |
| FD&C Blue #1 | 0.0117% |

Part (II):

| hydrogen peroxide, 50% aq. | 6.0000% |
|---|---|
| dodecylbenzene sulfonic acid, sodium salt | 0.2000% |
| dipicolinic acid | 0.0500% |

(pH adjusted to 2.65 with NaOH)

The in situ peracid generator combined: Part (I) 3.5% of a 50% $H_2O_2$ and Part (II) 96.5%. The two parts were blended together at about 20° C. The initial combination resulted in the FD&C blue dye mixing into the other solution, providing a visualization of mixing, followed by a rapid (30-60 seconds) transition from blue to green. The green color indicates the performic acid has reached a concentration of about 300 ppm (also indicative of the use solution reaching a lethal for C-diff spores). Following from about 48 to 72 hours from combination of the two-part system, both of the yellow dyes and the FD&C blue dye fade, indicating the useful life of product has expired.

Example 2

The self-indicating peroxycarboxylic acid chemistry formula of Example 1 was produced as described as a two part mixture followed by several seconds of mixing and immediate placement in the 1 cm cell. Scans were run at 30 second intervals beginning immediately.

FIG. 1 shows a graph of a UV-VIS scans at 30 second intervals showing respective absorptions of the dyes employed for the self-indicating chemistry for use with the peroxycarboxylic acid compositions. As shown, the 410 nm peak grows with time (yellow indicator in the peracid composition) while the 620 nm peak (blue color indicator in the peracid composition) fades very slowly.

Example 3

The two-part chemistry system of was evaluated for its ability to provide self-indicating detection of changes in concentration of peroxycarboxylic acid concentrations in a solution produced in situ. In this example performic acid was generated in situ as the peroxycarboxylic acid composition.

Ester Pre-Mix:

| Ethyl formate | 57.0000% |
|---|---|
| Glyceryl triformate | 41.6559% |
| Imidazole | 1.2900% |
| TMB | 0.0200% |
| ABTS | 0.0317% |
| FD&C Blue #1 | 0.0024% |

The pre-mix was added in the quantity of 3.5 g to 97.0 g of a 3% hydrogen peroxide solution. The final latent peracid selective dyes and background dye were present at the following use levels:

Use Levels

| Description | wt % | ppm (w/w) |
|---|---|---|
| TMB | 0.00060 | 6.0 |
| ABTS | 0.00095 | 9.5 |
| FD&C Blue #1 | 0.00007 | 0.7 |

Beneficially, the in situ peracid generator resulted in the FD&C blue dye mixing into the other solution, providing a visualization of mixing, followed by a rapid transition from blue to green. The green color indicates the performic acid has reached a concentration of about 300 ppm (also indicative of the use solution reaching a lethal for C-diff spores). Following from about 48 to 72 hours from combination of the two-part system, both of the yellow dyes and the FD&C blue dye fade, indicating the useful life of product has expired.

Example 4

Figure 2:
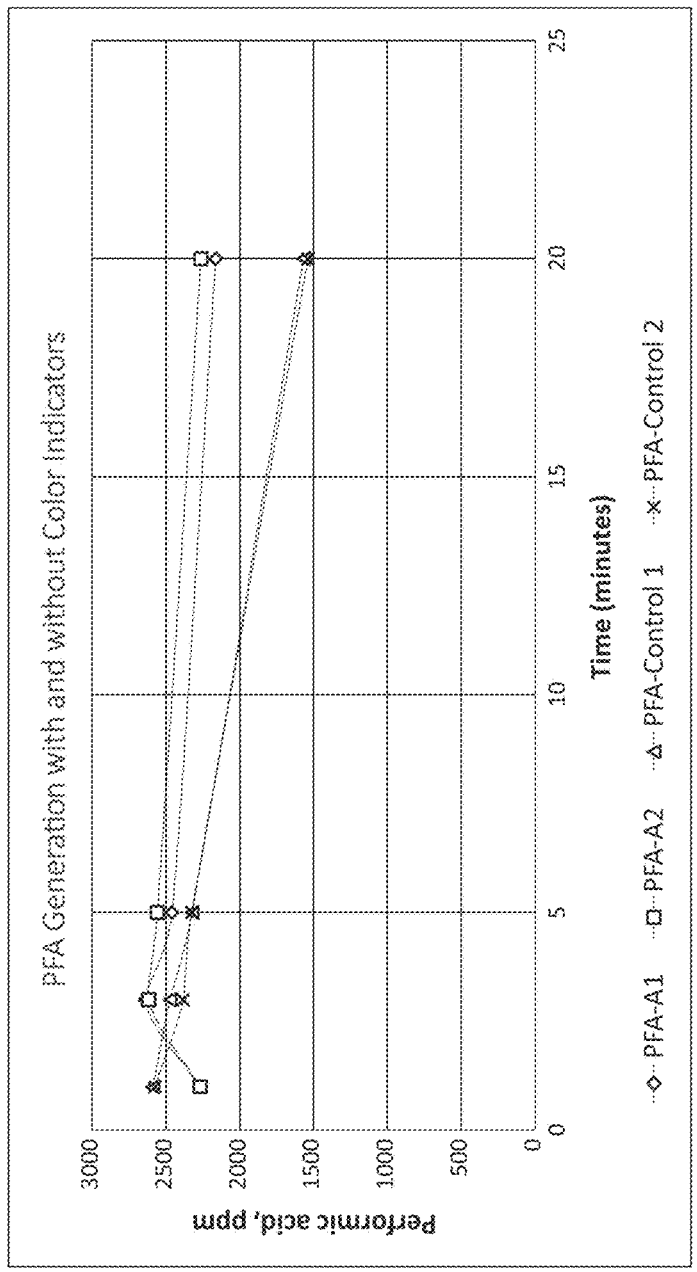
FIG. 2 shows a graph of measured peroxyformic acid concentration over time (20 minutes) depicting a stabilizing effect of the visual indicator system according to embodiments of the invention on performic acid.

The self-indicating chemistry system was further evaluated to confirm the non-destructive nature of the self-indicating systems on the peracid compositions employed for antimicrobial and other applications of use. In this example the extent of destruction of the peracid concentration was evaluated as a result of the interaction with the dyes of the indicating systems. The concentration of peroxyformic acid was evaluated over time (up to 20 minutes) after addition of the color dyes, as shown in FIG. 2. Surprisingly, as shown in the graph of FIG. 2 the dyes have a stabilizing effect on the peracid.

The evaluated formulations are shown below:
PFA Part (I): Dye

| Glyceryl formate | 97.0643% |
|---|---|
| Imidazole | 2.7964% |
| 3,3',5,5'-Tetramethylbenzidine (TMB) | 0.0513% |
| 2,2'-azino-bis(3-ethylbenzothiazoline-6-sulphonic acid) (ABTS) | 0.0766% |
| FD&C Blue #1 | 0.0115% |

PFA Part (II): Peroxide Activator

| hydrogen peroxide, 50% aq. | 96.0025% |
|---|---|
| dodecylbenzene sulfonic acid, sodium salt | 3.2001% |
| dipicolinic acid | 0.7975% |

(pH adjusted to 2.65 with NaOH)

The on-site peracid generation was tested combining 3.5 wt-% Part I (dye) and 96.5 wt-% Part II (peroxide activator).

Control Part (I): Dye

| Glyceryl formate | 94.5267% |
|---|---|
| Imidazole | 5.4733% |

No dyes present

Control Part (II): Peroxide Activator

| hydrogen peroxide, 50% aq. | 96.0025% |
|---|---|
| dodecylbenzene sulfonic acid, sodium salt | 3.2001% |
| dipicolinic acid | 0.7975% |

(pH adjusted to 2.65 with NaOH)

The on-site peracid generation for the control was tested combining 3.5 wt-% Part I (control-no dye) and 96.5 wt-% Part II (peroxide activator).

The data depicted in FIG. 2 is shown in Table 2.

TABLE 2

| Time (min) | PFA-A1 (ppm) | PFA-A2 (ppm) | PFA-Control 1 (ppm) | PFA-Control 2 (ppm) |
|---|---|---|---|---|
| 1 | 2273 | 2268 | 2589 | 2577 |
| 3 | 2642 | 2618 | 2473 | 2382 |
| 5 | 2459 | 2558 | 2325 | 2325 |

TABLE 2-continued

| Time (min) | PFA-A1 (ppm) | PFA-A2 (ppm) | PFA-Control 1 (ppm) | PFA-Control 2 (ppm) |
|---|---|---|---|---|
| 20 | 2164 | 2264 | 1566 | 1535 |
| 47 | 1691 | 1683 | | |

Example 5

The self-indicating chemistry system was further evaluated to assess the half-lives of exemplary latent and pre-existing dyes suitable for use according to embodiments of the invention, as shown in Table 3.

TABLE 3

| pre-existing or latent dyes | Dye Conc. (ppm) | λ max (nm) | Max Absorbance | Half-Life of Dyes (minutes at 20° C.) |
|---|---|---|---|---|
| TMB | 233 | 410-420 | 0.40 | 3 |
| ABTS | 374 | 410-421 | 0.34 | 420 |
| FD&C Blue #1 | 55 | 630 | 0.25 | 60 |

| Performic Generating Portion: | wt. % |
|---|---|
| Formyl glyceride(s) | 1.5 |
| Hydrogen peroxide | 3 |

| Adjuvants: | Conc., ppm |
|---|---|
| Imidazole | 236 |
| DDBSA | 2000 |
| Dipicolinic acid | 500 |

Figure 3:
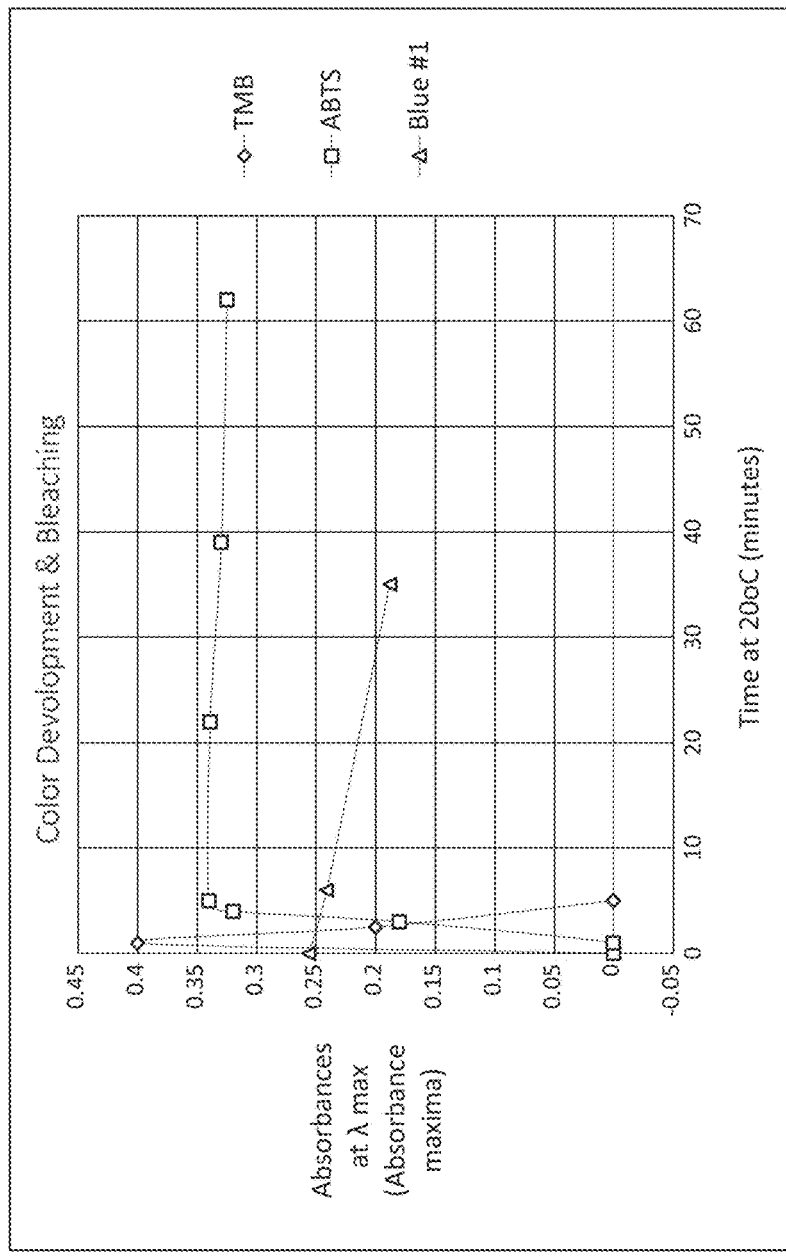
FIG. 3 shows a graph of measured half-lives of preferred dyes for the self-indicating chemistry compositions as referred to as a degeneration graph according to embodiments of the invention on performic acid.

Further experimentation of the combination of components shown in Table 3 was evaluated. When the yellow TMB signal is generated and mixed with the first yellow dye formed, "oxidized" TMB, and later "oxidized": ABTS the result is a bright green (as can be readily interpreted as a visual "ready" signal) due to mixing of yellow with the pre-existing blue. For the dyes in Table 3 after approximately 60 minutes the pre-existing blue fades while the developed yellow from the more rugged latent dye of ABTS becomes dominant in the mixture. The resulting dominant color of yellow may be interpreted as a readily interpreted visual "warning" of peracid exhaustion, providing desirable visual indicators of the concentration of the peracid composition concentration. A visual depiction of this color development and bleackign or oxidizing is shown in FIG. 3.

The inventions being thus described, it will be obvious that the same may be varied in many ways. Such variations are not to be regarded as a departure from the spirit and scope of the inventions and all such modifications are intended to be included within the scope of the following claims. The above specification provides a description of the manufacture and use of the disclosed compositions and methods. Since many embodiments can be made without departing from the spirit and scope of the invention, the invention resides in the claims.

What is claimed is:

1. A self-indicating peroxycarboxylic acid chemistry composition comprising:
   a peroxycarboxylic acid;
   a background dye comprising FD&C Blue No. 1;
   at least one latent peracid-selective dye, wherein said at least one peracid-selective dye is a horseradish peroxidase (HRP) substrate, which upon oxidation by the peroxycarboxylic acid, provides a visual indication of the presence of a minimum concentration of peroxycarboxylic acid for efficacy as an antimicrobial; and
   wherein the composition is free of iodide.

2. The composition of claim 1, wherein the combination of dyes have different half-lives to provide sustained visual indication of peroxycarboxylic acid concentration for at least 12 hours.

3. The composition of claim 1, wherein the HRP substrate is p-Nitrophenyl Phosphate, Disodium Salt, 2,2″-Azinobis [3-ethylbenzothiazoline-6-sulfonic acid]-diammonium salt, o-phenylenediamine dihydrochloride, 3,3',5,5'-tetramethylbenzidine, or combinations thereof.

4. The composition of claim 1, wherein the background dye is produced using aromatic hydrocarbons from petroleum.

5. The composition of claim 1, wherein the latent dye is non-destructive to the peroxycarboxylic acid and/or provides at least about 10% improvement in peroxycarboxylic acid stabilization in comparison to a peroxycarboxylic acid composition not employing the dye as measured by concentration (ppm) of the peroxycarboxylic acid retained in the composition over at least 10 minutes.

6. The composition of claim 1, wherein the peroxycarboxylic acid is a C1-C18 peroxycarboxylic acid.

7. The composition of claim 1, wherein the latent dyes provide a tri-color indicator system.

8. The composition of claim 1, further comprising at least one additional functional ingredient selected from the group consisting of a catalyst, stabilizing agent, pH buffering agent, acidulant, defoaming agent, anti-redeposition agent, bleaching agent, solubility modifier, dispersant, wetting agent, metal protecting agent, corrosion inhibitor, additional sequestrant and/or chelating agent, fragrance, dye, rheology modifier or thickener, hydrotrope or coupler, solvent and combinations thereof.

* * * * *

UNITED STATES PATENT AND TRADEMARK OFFICE
CERTIFICATE OF CORRECTION

PATENT NO. : 10,285,401 B2
APPLICATION NO. : 15/260760
DATED : May 14, 2019
INVENTOR(S) : David D. McSherry, Junzhong Li and Richard Staub It is certified that error appears in the above-identified patent and that said Letters Patent is hereby corrected as shown below:

In the Claims

In Claim 3, Column 34, Line 26:
DELETE: "2,2''"
INSERT: --2,2'--

Signed and Sealed this
Twenty-seventh Day of August, 2019

Andrei Iancu
*Director of the United States Patent and Trademark Office*